United States Patent [19]

Dower et al.

[11] Patent Number: 5,081,228
[45] Date of Patent: Jan. 14, 1992

[54] INTERLEUKIN-1 RECEPTORS

[75] Inventors: Steven K. Dower, Redmond; Carl J. March, Seattle; John E. Sims, Seattle; David L. Urdal, Seattle, all of Wash.

[73] Assignee: Immunex Corporation, Seattle, Wash.

[21] Appl. No.: 258,756

[22] Filed: Oct. 13, 1988

Related U.S. Application Data

[63] Continuation-in-part of Ser. No. 160,550, Feb. 25, 1988, Pat. No. 4,968,607, which is a continuation-in-part of Ser. No. 125,627, Nov. 25, 1987, abandoned.

[51] Int. Cl.$^5$ .................. C07K 13/00; A61K 37/02
[52] U.S. Cl. .................. 530/35.1; 530/350; 530/395; 530/820; 435/69.5; 435/69.1; 424/85.1; 424/85.2; 514/2; 514/8
[58] Field of Search .............. 530/351, 350, 395, 820; 435/68, 70; 514/2, 8; 424/85.1, 85.2

[56] References Cited

PUBLICATIONS

Perlman et al., *J. Mol. Biol.*, 167, 1983, pp. 391–402.
Introduction to Proteins and Protein Engineering, ed. Robinson et al. (Elsevier) 1986, pp. 258–259.
Bron et al., *FEBS* 219(2) 1987, pp. 365–368.
Bonin et al., *JBC* 263(23) 1988, pp. 11052–11055.
Palaszynski, *Biochem Biophy Res Conv* 147(1) 1987, pp. 204–211.
Kroggel et al., *FEBS* 229(1) 1988, pp. 59–62.
Horuk et al., *Prog Leukocyte Biol* 8, 1988, pp. 179–184.

*Primary Examiner*—Garnette D. Draper
*Attorney, Agent, or Firm*—Scott G. Hallquist; Christopher L. Wight; David D. McMasters

[57] ABSTRACT

Mammalian Interleukin-1 receptor proteins (IL-1Rs), DNAs and expression vectors encoding mammalian IL-1Rs, and processes for producing mammalian IL-1Rs as products of cell culture, including recombinant systems, are disclosed.

20 Claims, 14 Drawing Sheets

```
   1  5'-TGGGTCGTCT GACTAGAAGT GAGCTGTCTG TCATTCTTGT GCACGCCAGC
  51     CCAGTAATCA TTTGGAGGCA AAGCAAACTG TAAGTAATGC TGTCCTGGGC
 101     TGACTTGAGG AGGCAGTTTT CGTTTTAACA GCCAGTGTTT ATTTGCTCAG
 151     CAAACGTTGT CTCGGGGAGA AATGTCGCTG GATGTCATCA GAGTTCCCAG
 201     TGCCCCGAAC CGTGAACAAC ACAAATGGAG AATATGAAAG TGCTACTGGG
 251     GCTCATTTGT CTCATGGTGC CTCTGCTGTC GCTGGAGATT GACGTATGTA
 301     CAGAATATCC AAATCAGATC GTTTTGTTTT TATCTGTAAA TGAAATTGAT
 351     ATTCGCAAGT GTCCTCTTAC TCCAAATAAA ATGCACGGCG ACACCATAAT
 401     TTGGTACAAG AATGACAGCA AGACCCCCAT ATCAGCGGAC CGGGACTCCA
 451     GGATTCATCA GCAGAATGAA CATCTTTGGT TTGTACCTGC CAAGGTGGAG
 501     GACTCAGGAT ATTACTATTG TATAGTAAGA AACTCAACTT ACTGCCTCAA
 551     AACTAAAGTA ACCGTAACTG TGTTAGAGAA TGACCCTGGC TTGTGTTACA
 601     GCACACAGGC CACCTTCCCA CAGCGGCTCC ACATTGCCGG GGATGGAAGT
 651     CTTGTGTGCC CTTATGTGAG TTATTTTAAA GATGAAAATA ATGAGTTACC
 701     CGAGGTCCAG TGGTATAAGA ACTGTAAACC TCTGCTTCTT GACAACGTGA
 751     GCTTCTTCGG AGTAAAAGAT AAACTGTTGG TGAGGAATGT GGCTGAAGAG
 801     CACAGAGGGG ACTATATATG CCGTATGTCC TATACGTTCC GGGGGAAGCA
 851     ATATCCGGTC ACACGAGTAA TACAATTTAT CACAATAGAT GAAAACAAGA
 901     GGGACAGACC TGTTATCCTG AGCCCTCGGA ATGAGACGAT CGAAGCTGAC
 951     CCAGGATCAA TGATACAACT GATCTGCAAC GTCACGGGCC AGTTCTCAGA
1001     CCTTGTCTAC TGGAAGTGGA ATGGATCAGA AATTGAATGG AATGATCCAT
1051     TTCTAGCTGA AGACTATCAA TTTGTGGAAC ATCCTTCAAC CAAAAGAAAA
1101     TACACACTCA TTACAACACT TAACATTTCA GAAGTTAAAA GCCAGTTTTA
1151     TCGCTATCCG TTTATCTGTG TTGTTAAGAA CACAAATATT TTTGAGTCGG
1201     CGCATGTGCA GTTAATATAC CCAGTCCCTG ACTTCAAGAA TTACCTCATC
1251     GGGGGCTTTA TCATCCTCAC GGCTACAATT GTATGCTGTG TGTGCATCTA
1301     TAAAGTCTTC AAGGTTGACA TAGTGCTTTG GTACAGGGAC TCCTGCTCTG
1351     GTTTTCTTCC TTCAAAAGCT TCAGATGGAA AGACATACGA TGCCTATATT
1401     CTTTATCCCA AGACCCTGGG AGAGGGGTCC TTCTCAGACT TAGATACTTT
1451     TGTTTTTAAA CTGTTGCCTG AGGTCTTGGA GGGACAGTTT GGATACAAGC
1501     TGTTCATTTA TGGAAGGGAT GACTATGTTG GAGAAGATAC CATCGAGGTT
1551     ACTAATGAAA ATGTAAAGAA AAGCAGGAGG CTGATTATCA TTCTAGTGAG
1601     AGATATGGGA GGCTTCAGCT GGCTGGGCCA GTCATCTGAA GAGCAAATAG
1651     CCATATACAA TGCTCTCATC CAGGAAGGAA TTAAAATCGT CCTGCTTGAG
1701     TTGGAGAAAA TCCAAGACTA TGAGAAAATG CCAGATTCTA TTCAGTTCAT
1751     TAAGCAGAAA CACGGAGTCA TTTGCTGGTC AGGAGACTTT CAAGAAAGAC
1801     CACAGTCTGC AAAGACCAGG TTCTGGAAAA ACTTAAGATA CCAGATGCCA
1851     GCCCAACGGA GATCACCATT GTCTAAACAC CGCTTACTAA CCCTGGATCC
1901     TGTGCGGGAC ACTAAGGAGA AACTGCCGGC AGCAACACAC TTACCACTCG
1951     GCTAGCATGG CAAAAGTGGG CAGGCCAAGA ACTTCGGAAT ATCTCCCATC
2001     ATAAGAGGCT GCAGCTGGGC TGTGCCTCCC AGTAAAACAG TCACGAACCA
2051     AACCTGTGCA GTCCCTTGTT CCAGATCACC TGGAACTGGA TTGGGAAGAG
2101     AACAGGACTT GGTGGCCAGG ACCGCTCAGA GAGCCATGGT TGCTCAGGGA
2151     TGCTGCTCCG GGATGCTTGA CTAACAGTCG AGGCAGTGAA CTGGGTGTAG
2201     AAAGCGTCAG GAAATGGCCA CATGTGTGGA TGGTTTAATT AGATTCTGTG
2251     GAGTCTCACA GTGGGATTGT GGCTGTCTGA GGACACTTTG GGGGTCGCT
2301     GTCCAAGAAG TGGCTCCCCA AGTATAAGT GCGGGTGAGG TTTACTGATA
2351     CCCCAC-3'
```

Figure 2

```
5'-ATG GAG AAT ATG AAA GTG CTA CTG GGG CTC ATT TGT CTC ATG GTG    -15
   Met Glu Asn Met Lys Val Leu Leu Gly Leu Ile Cys Leu Met Val     -5

CCT CTG CTG TCG CTG GAG ATT GAC GTA TGT ACA GAA TAT CCA AAT     33
   Pro Leu Leu Ser Leu Glu Ile Asp Val Cys Thr Glu Tyr Pro Asn     11

CAG ATC GTT TTG TTT TTA TCT GTA AAT GAA ATT GAT ATT CGC AAG     78
   Gln Ile Val Leu Phe Leu Ser Val Asn Glu Ile Asp Ile Arg Lys     26

TGT CCT CTT ACT CCA AAT AAA ATG CAC GGC GAC ACC ATA ATT TGG    123
   Cys Pro Leu Thr Pro Asn Lys Met His Gly Asp Thr Ile Ile Trp     41

TAC AAG AAT GAC AGC AAG ACC CCC ATA TCA GCG GAC CGG GAC TCC    168
   Tyr Lys Asn Asp Ser Lys Thr Pro Ile Ser Ala Asp Arg Asp Ser     56

AGG ATT CAT CAG CAG AAT GAA CAT CTT TGG TTT GTA CCT GCC AAG    213
   Arg Ile His Gln Gln Asn Glu His Leu Trp Phe Val Pro Ala Lys     71

GTG GAG GAC TCA GGA TAT TAC TAT TGT ATA GTA AGA AAC TCA ACT    258
   Val Glu Asp Ser Gly Tyr Tyr Tyr Cys Ile Val Arg Asn Ser Thr     86

TAC TGC CTC AAA ACT AAA GTA ACC GTA ACT GTG TTA GAG AAT GAC    303
   Tyr Cys Leu Lys Thr Lys Val Thr Val Thr Val Leu Glu Asn Asp    101

CCT GGC TTG TGT TAC AGC ACA CAG GCC ACC TTC CCA CAG CGG CTC    348
   Pro Gly Leu Cys Tyr Ser Thr Gln Ala Thr Phe Pro Gln Arg Leu    116

CAC ATT GCC GGG GAT GGA AGT CTT GTG TGC CCT TAT GTG AGT TAT    393
   His Ile Ala Gly Asp Gly Ser Leu Val Cys Pro Tyr Val Ser Tyr    131

TTT AAA GAT GAA AAT AAT GAG TTA CCC GAG GTC CAG TGG TAT AAG    438
   Phe Lys Asp Glu Asn Asn Glu Leu Pro Glu Val Gln Trp Tyr Lys    146

AAC TGT AAA CCT CTG CTT CTT GAC AAC GTG AGC TTC TTC GGA GTA    483
   Asn Cys Lys Pro Leu Leu Leu Asp Asn Val Ser Phe Phe Gly Val    161

AAA GAT AAA CTG TTG GTG AGG AAT GTG GCT GAA GAG CAC AGA GGG    528
   Lys Asp Lys Leu Leu Val Arg Asn Val Ala Glu Glu His Arg Gly    176

GAC TAT ATA TGC CGT ATG TCC TAT ACG TTC CGG GGG AAG CAA TAT    573
   Asp Tyr Ile Cys Arg Met Ser Tyr Thr Phe Arg Gly Lys Gln Tyr    191

CCG GTC ACA CGA GTA ATA CAA TTT ATC ACA ATA GAT GAA AAC AAG    618
   Pro Val Thr Arg Val Ile Gln Phe Ile Thr Ile Asp Glu Asn Lys    206
```

*Figure 3A*

```
AGG GAC AGA CCT GTT ATC CTG AGC CCT CGG AAT GAG ACG ATC GAA    663
Arg Asp Arg Pro Val Ile Leu Ser Pro Arg Asn Glu Thr Ile Glu    221

GCT GAC CCA GGA TCA ATG ATA CAA CTG ATC TGC AAC GTC ACG GGC    708
Ala Asp Pro Gly Ser Met Ile Gln Leu Ile Cys Asn Val Thr Gly    236

CAG TTC TCA GAC CTT GTC TAC TGG AAG TGG AAT GGA TCA GAA ATT    753
Gln Phe Ser Asp Leu Val Tyr Trp Lys Trp Asn Gly Ser Glu Ile    251

GAA TGG AAT GAT CCA TTT CTA GCT GAA GAC TAT CAA TTT GTG GAA    798
Glu Trp Asn Asp Pro Phe Leu Ala Glu Asp Tyr Gln Phe Val Glu    266

CAT CCT TCA ACC AAA AGA AAA TAC ACA CTC ATT ACA ACA CTT AAC    843
His Pro Ser Thr Lys Arg Lys Tyr Thr Leu Ile Thr Thr Leu Asn    281

ATT TCA GAA GTT AAA AGC CAG TTT TAT CGC TAT CCG TTT ATC TGT    888
Ile Ser Glu Val Lys Ser Gln Phe Tyr Arg Tyr Pro Phe Ile Cys    296

GTT GTT AAG AAC ACA AAT ATT TTT GAG TCG GCG CAT GTG CAG TTA    933
Val Val Lys Asn Thr Asn Ile Phe Glu Ser Ala His Val Gln Leu    311

ATA TAC CCA GTC CCT GAC TTC AAG AAT TAC CTC ATC GGG GGC TTT    978
Ile Tyr Pro Val Pro Asp Phe Lys Asn Tyr Leu Ile Gly Gly Phe    326

ATC ATC CTC ACG GCT ACA ATT GTA TGC TGT GTG TGC ATC TAT AAA    1023
Ile Ile Leu Thr Ala Thr Ile Val Cys Cys Val Cys Ile Tyr Lys    341

GTC TTC AAG GTT GAC ATA GTG CTT TGG TAC AGG GAC TCC TGC TCT    1068
Val Phe Lys Val Asp Ile Val Leu Trp Tyr Arg Asp Ser Cys Ser    356

GGT TTT CTT CCT TCA AAA GCT TCA GAT GGA AAG ACA TAC GAT GCC    1113
Gly Phe Leu Pro Ser Lys Ala Ser Asp Gly Lys Thr Tyr Asp Ala    371

TAT ATT CTT TAT CCC AAG ACC CTG GGA GAG GGG TCC TTC TCA GAC    1158
Tyr Ile Leu Tyr Pro Lys Thr Leu Gly Glu Gly Ser Phe Ser Asp    386

TTA GAT ACT TTT GTT TTT AAA CTG TTG CCT GAG GTC TTG GAG GGA    1203
Leu Asp Thr Phe Val Phe Lys Leu Leu Pro Glu Val Leu Glu Gly    401

CAG TTT GGA TAC AAG CTG TTC ATT TAT GGA AGG GAT GAC TAT GTT    1248
Gln Phe Gly Tyr Lys Leu Phe Ile Tyr Gly Arg Asp Asp Tyr Val    416

GGA GAA GAT ACC ATC GAG GTT ACT AAT GAA AAT GTA AAG AAA AGC    1293
Gly Glu Asp Thr Ile Glu Val Thr Asn Glu Asn Val Lys Lys Ser    431
```

Figure 3B

```
AGG AGG CTG ATT ATC ATT CTA GTG AGA GAT ATG GGA GGC TTC AGC    1338
Arg Arg Leu Ile Ile Ile Leu Val Arg Asp Met Gly Gly Phe Ser     446

TGG CTG GGC CAG TCA TCT GAA GAG CAA ATA GCC ATA TAC AAT GCT    1383
Trp Leu Gly Gln Ser Ser Glu Glu Gln Ile Ala Ile Tyr Asn Ala     461

CTC ATC CAG GAA GGA ATT AAA ATC GTC CTG CTT GAG TTG GAG AAA    1428
Leu Ile Gln Glu Gly Ile Lys Ile Val Leu Leu Glu Leu Glu Lys     476

ATC CAA GAC TAT GAG AAA ATG CCA GAT TCT ATT CAG TTC ATT AAG    1473
Ile Gln Asp Tyr Glu Lys Met Pro Asp Ser Ile Gln Phe Ile Lys     491

CAG AAA CAC GGA GTC ATT TGC TGG TCA GGA GAC TTT CAA GAA AGA    1518
Gln Lys His Gly Val Ile Cys Trp Ser Gly Asp Phe Gln Glu Arg     506

CCA CAG TCT GCA AAG ACC AGG TTC TGG AAA AAC TTA AGA TAC CAG    1563
Pro Gln Ser Ala Lys Thr Arg Phe Trp Lys Asn Leu Arg Tyr Gln     521

ATG CCA GCC CAA CGG AGA TCA CCA TTG TCT AAA CAC CGC TTA CTA    1608
Met Pro Ala Gln Arg Arg Ser Pro Leu Ser Lys His Arg Leu Leu     536

ACC CTG GAT CCT GTG CGG GAC ACT AAG GAG AAA CTG CCG GCA GCA    1653
Thr Leu Asp Pro Val Arg Asp Thr Lys Glu Lys Leu Pro Ala Ala     551

ACA CAC TTA CCA CTC GGC TAG-3'                                  1671
Thr His Leu Pro Leu Gly End                                      557
```

*Figure 3C*

```
   1 5'-AGACGCACCC TCTGAAGATG GTGGACTCCC TCCTGAGAAG CTGGGACCCC
  51    TTGGTAAAAG ACAAGGCCTT CTCCAAGAAG AATATGAAAG TGTTACTCAG
 101    ACTTATTTGT TTCATAGCTC TACTGATTTC TTCTCTGGAG GCTGATAAAT
 151    GCAAGGAACG TGAAGAAAAA ATAATTTTAG TGTCATCTGC AAATGAAATT
 201    GATGTTCGTC CCTGTCCTCT TAACCCAAAT GAACACAAAG GCACTATAAC
 251    TTGGTATAAA GATGACAGCA AGACACCTGT ATCTACAGAA CAAGCCTCCA
 301    GGATTCATCA ACACAAAGAG AAACTTTGGT TTGTTCCTGC TAAGGTGGAG
 351    GATTCAGGAC ATTACTATTG CGTGGTAAGA AATTCATCTT ACTGCCTCAG
 401    AATTAAAATA AGTGCAAAAT TTGTGGAGAA TGAGCCTAAC TTATGTTATA
 451    ATGCACAAGC CATATTTAAG CAGAAACTAC CCGTTGCAGG AGACGGAGGA
 501    CTTGTGTGCC CTTATATGGA GTTTTTTAAA AATGAAAATA ATGAGTTACC
 551    TAAATTACAG TGGTATAAGG ATTGCAAACC TCTACTTCTT GACAATATAC
 601    ACTTTAGTGG AGTCAAAGAT AGGCTCATCG TGATGAATGT GGCTGAAAAG
 651    CATAGAGGGA ACTATACTTG TCATGCATCC TACACATACT TGGGCAAGCA
 701    ATATCCTATT ACCCGGGTAA TAGAATTTAT TACTCTAGAG GAAAACAAAC
 751    CCACAAGGCC TGTGATTGTG AGCCCAGCTA ATGAGACAAT GGAAGTAGAC
 801    TTGGGATCCC AGATACAATT GATCTGTAAT GTCACCGGCC AGTTGAGTGA
 851    CATTGCTTAC TGGAAGTGGA ATGGGTCAGT AATTGATGAA GATGACCCAG
 901    TGCTAGGGGA AGACTATTAC AGTGTGGAAA ATCCTGCAAA CAAAAGAAGG
 951    AGTACCCTCA TCACAGTGCT TAATATATCG GAAATTGAAA GTAGATTTTA
1001    TAAACATCCA TTTACCTGTT TTGCCAAGAA TACACATGGT ATAGATGCAG
1051    CATATATCCA GTTAATATAT CCAGTCACTA ATTTCCAGAA GCACATGATT
1101    GGTATATGTG TCACGTTGAC AGTCATAATT GTGTGTTCTG TTTTCATCTA
1151    TAAAATCTTC AAGATTGACA TTGTGCTTTG GTACAGGGAT TCCTGCTATG
1201    ATTTTCTCCC AATAAAAGCT TCAGATGGAA AGACCTATGA CGCATATATA
1251    CTGTATCCAA AGACTGTTGG GGAAGGGTCT ACCTCTGACT GTGATATTTT
1301    TGTGTTTAAA GTCTTGCCTG AGGTCTTGGA AAAACAGTGT GGATATAAGC
1351    TGTTCATTTA TGGAAGGGAT GACTACGTTG GGGAAGACAT TGTTGAGGTC
1401    ATTAATGAAA ACGTAAAGAA AAGCAGAAGA CTGATTATCA TTTTAGTCAG
1451    AGAAACATCA GGCTTCAGCT GGCTGGGTGG TTCATCTGAA GAGCAAATAG
1501    CCATGTATAA TGCTCTTGTT CAGGATGGAA TTAAAGTTGT CCTGCTTGAG
1551    CTGGAGAAAA TCCAAGACTA TGAGAAAATG CCAGAATCGA TTAAATTCAT
1601    TAAGCAGAAA CATGGGGCTA TCCGCTGGTC AGGGGACTTT ACACAGGGAC
1651    CACAGTCTGC AAAGACAAGG TTCTGGAAGA ATGTCAGGTA CCACATGCCA
1701    GTCCAGCGAC GGTCACCTTC ATCTAAACAC CAGTTACTGT CACCAGCCAC
1751    TAAGGAGAAA CTGCAAAGAG AGGCTCACGT GCCTCTCGGG TAGCATGGAG
1801    AAGTTGCCAA GAGTTCTTTA GGTGCCTCCT GTCTTATGGC GTTGCAGGCC
1851    AGGTTATGCC TCATGCTGAC TTGCAGAGTT CATGGAATGT AACTATATCA
1901    TCCTTTATCC CTGAGGTCAC CTGGAATCAG ATTATTAAGG GAATAAGCCA
1951    TGACGTCAAT AGCAGCCCAG GGCACTTCAG AGTAGAGGGC TTGGGAAGAT
2001    CTTTTAAAAA GGCAGTAGGC CCGGTGTGGT GGCTCACGCC TATAATCCCA
2051    GCACTTTGGG AGGCTGAAGT GGGTGGATCA CCAGAGGTCA GGAGTTCGAG
2101    ACCAGCCCAG CCAACATGGC AAAACCCCAT CTCTACTAAA AATACAAAAA
2151    TGAGCTAGGC ATGGTGGCAC ACGCCTGTAA TCCCAGCTAC ACCTGAGGCT
2201    GAGGCAGGAG AATTGCTTGA ACCGGGGAGA CGGAGGTTGC AGTGAGCCGA
2301    GTTTGGGCCA CTGCACTCTA GCCTGGCAAC AGAGCAAGAC TCCGTCTCAA
2351    AAAAAGGGCA ATAAATGCCC TCTCTGAATG TTTGAACTGC CAAGAAAAGG
2401    CATGGAGACA GCGAACTAGA AGAAAGGGCA AGAAGGAAAT AGCCACCGTC
2451    TACAGATGGC TTAGTTAAGT CATCCACAGC CCAAGGGCGG CGGCTATGCC
2501    TTGTCTGGGG ACCCTGTAGA GTCACTGACC CTGGAGCGGC TCTCCTGAGA
2551    GGTGCTGCAG GCAAAGTGAG ACTGACACCT CACTGAGGAA GGGAGACATA
2601    TTCTTGGAGA ACTTTCCATC TGCTTGTATT TTCCATACAC ATCCCCAGCC-3'
```

Figure 4

```
ATG AAA GTG TTA CTC AGA CTT ATT TGT TTC ATA GCT CTA CTG ATT     -9
Met Lys Val Leu Leu Arg Leu Ile Cys Phe Ile Ala Leu Leu Ile     -3

TCT TCT CTG GAG GCT GAT AAA TGC AAG GAA CGT GAA GAA AAA ATA     39
Ser Ser Leu Glu Ala Asp Lys Cys Lys Glu Arg Glu Glu Lys Ile     13

ATT TTA GTG TCA TCT GCA AAT GAA ATT GAT GTT CGT CCC TGT CCT     84
Ile Leu Val Ser Ser Ala Asn Glu Ile Asp Val Arg Pro Cys Pro     28

CTT AAC CCA AAT GAA CAC AAA GGC ACT ATA ACT TGG TAT AAA GAT     129
Leu Asn Pro Asn Glu His Lys Gly Thr Ile Thr Trp Tyr Lys Asp     43

GAC AGC AAG ACA CCT GTA TCT ACA GAA CAA GCC TCC AGG ATT CAT     174
Asp Ser Lys Thr Pro Val Ser Thr Glu Gln Ala Ser Arg Ile His     58

CAA CAC AAA GAG AAA CTT TGG TTT GTT CCT GCT AAG GTG GAG GAT     219
Gln His Lys Glu Lys Leu Trp Phe Val Pro Ala Lys Val Glu Asp     73

TCA GGA CAT TAC TAT TGC GTG GTA AGA AAT TCA TCT TAC TGC CTC     264
Ser Gly His Tyr Tyr Cys Val Val Arg Asn Ser Ser Tyr Cys Leu     88

AGA ATT AAA ATA AGT GCA AAA TTT GTG GAG AAT GAG CCT AAC TTA     309
Arg Ile Lys Ile Ser Ala Lys Phe Val Glu Asn Glu Pro Asn Leu     103

TGT TAT AAT GCA CAA GCC ATA TTT AAG CAG AAA CTA CCC GTT GCA     354
Cys Tyr Asn Ala Gln Ala Ile Phe Lys Gln Lys Leu Pro Val Ala     118

GGA GAC GGA GGA CTT GTG TGC CCT TAT ATG GAG TTT TTT AAA AAT     399
Gly Asp Gly Gly Leu Val Cys Pro Tyr Met Glu Phe Phe Lys Asn     133

GAA AAT AAT GAG TTA CCT AAA TTA CAG TGG TAT AAG GAT TGC AAA     444
Glu Asn Asn Glu Leu Pro Lys Leu Gln Trp Tyr Lys Asp Cys Lys     148

CCT CTA CTT CTT GAC AAT ATA CAC TTT AGT GGA GTC AAA GAT AGG     489
Pro Leu Leu Leu Asp Asn Ile His Phe Ser Gly Val Lys Asp Arg     163

CTC ATC GTG ATG AAT GTG GCT GAA AAG CAT AGA GGG AAC TAT ACT     534
Leu Ile Val Met Asn Val Ala Glu Lys His Arg Gly Asn Tyr Thr     178

TGT CAT GCA TCC TAC ACA TAC TTG GGC AAG CAA TAT CCT ATT ACC     579
Cys His Ala Ser Tyr Thr Tyr Leu Gly Lys Gln Tyr Pro Ile Thr     193

CGG GTA ATA GAA TTT ATT ACT CTA GAG GAA AAC AAA CCC ACA AGG     624
Arg Val Ile Glu Phe Ile Thr Leu Glu Glu Asn Lys Pro Thr Arg     208

CCT GTG ATT GTG AGC CCA GCT AAT GAG ACA ATG GAA GTA GAC TTG     669
Pro Val Ile Val Ser Pro Ala Asn Glu Thr Met Glu Val Asp Leu     223
```

*Figure 5A*

```
GGA TCC CAG ATA CAA TTG ATC TGT AAT GTC ACC GGC CAG TTG AGT    714
Gly Ser Gln Ile Gln Leu Ile Cys Asn Val Thr Gly Gln Leu Ser    238

GAC ATT GCT TAC TGG AAG TGG AAT GGG TCA GTA ATT GAT GAA GAT    759
Asp Ile Ala Tyr Trp Lys Trp Asn Gly Ser Val Ile Asp Glu Asp    253

GAC CCA GTG CTA GGG GAA GAC TAT TAC AGT GTG GAA AAT CCT GCA    804
Asp Pro Val Leu Gly Glu Asp Tyr Tyr Ser Val Glu Asn Pro Ala    268

AAC AAA AGA AGG AGT ACC CTC ATC ACA GTG CTT AAT ATA TCG GAA    849
Asn Lys Arg Arg Ser Thr Leu Ile Thr Val Leu Asn Ile Ser Glu    283

ATT GAA AGT AGA TTT TAT AAA CAT CCA TTT ACC TGT TTT GCC AAG    894
Ile Glu Ser Arg Phe Tyr Lys His Pro Phe Thr Cys Phe Ala Lys    298

AAT ACA CAT GGT ATA GAT GCA GCA TAT ATC CAG TTA ATA TAT CCA    939
Asn Thr His Gly Ile Asp Ala Ala Tyr Ile Gln Leu Ile Tyr Pro    313

GTC ACT AAT TTC CAG AAG CAC ATG ATT GGT ATA TGT GTC ACG TTG    984
Val Thr Asn Phe Gln Lys His Met Ile Gly Ile Cys Val Thr Leu    328

ACA GTC ATA ATT GTG TGT TCT GTT TTC ATC TAT AAA ATC TTC AAG    1029
Thr Val Ile Ile Val Cys Ser Val Phe Ile Tyr Lys Ile Phe Lys    343

ATT GAC ATT GTG CTT TGG TAC AGG GAT CCC TGC TAT GAT TTT CTC    1074
Ile Asp Ile Val Leu Trp Tyr Arg Asp Ser Cys Tyr Asp Phe Leu    358

CCA ATA AAA GCT TCA GAT GGA AAG ACC TAT GAC GCA TAT ATA CTG    1119
Pro Ile Lys Ala Ser Asp Gly Lys Thr Tyr Asp Ala Tyr Ile Leu    373

TAT CCA AAG ACT GTT GGG GAA GGG TCT ACC TCT GAC TGT GAT ATT    1164
Tyr Pro Lys Thr Val Gly Glu Gly Ser Thr Ser Asp Cys Asp Ile    388

TTT GTG TTT AAA GTC TTG CCT GAG GTC TTG GAA AAA CAG TGT GGA    1209
Phe Val Phe Lys Val Leu Pro Glu Val Leu Glu Lys Gln Cys Gly    403

TAT AAG CTG TTC ATT TAT GGA AGG GAT GAC TAC GTT GGG GAA GAC    1254
Tyr Lys Leu Phe Ile Tyr Gly Arg Asp Asp Tyr Val Gly Glu Asp    418

ATT GTT GAG GTC ATT AAT GAA AAC GTA AAG AAA AGC AGA AGA CTG    1299
Ile Val Glu Val Ile Asn Glu Asn Val Lys Lys Ser Arg Arg Leu    433

ATT ATC ATT TTA GTC AGA GAA ACA TCA GGC TTC AGC TGG CTG GGT    1344
Ile Ile Ile Leu Val Arg Glu Thr Ser Gly Phe Ser Trp Leu Gly    448

GGT TCA TCT GAA GAG CAA ATA GCC ATG TAT AAT GCT CTT GTT CAG    1389
Gly Ser Ser Glu Glu Gln Ile Ala Met Tyr Asn Ala Leu Val Gln    463

GAT GGA ATT AAA GTT GTC CTG CTT GAG CTG GAG AAA ATC CAA GAC    1434
Asp Gly Ile Lys Val Val Leu Leu Glu Leu Glu Lys Ile Gln Asp    478
```

*Figure 5B*

```
TAT GAG AAA ATG CCA GAA TCG ATT AAA TTC ATT AAG CAG AAA CAT    1479
Tyr Glu Lys Met Pro Glu Ser Ile Lys Phe Ile Lys Gln Lys His     493

GGG GCT ATC CGC TGG TCA GGG GAC TTT ACA CAG GGA CCA CAG TCT    1524
Gly Ala Ile Arg Trp Ser Gly Asp Phe Thr Gln Gly Pro Gln Ser     508

GCA AAG ACA AGG TTC TGG AAG AAT GTC AGG TAC CAC ATG CCA GTC    1569
Ala Lys Thr Arg Phe Trp Lys Asn Val Arg Tyr His Met Pro Val     523

CAG CGA CGG TCA CCT TCA TCT AAA CAC CAG TTA CTG TCA CCA GCC    1614
Gln Arg Arg Ser Pro Ser Ser Lys His Gln Leu Leu Ser Pro Ala     538

ACT AAG GAG AAA CTG CAA AGA GAG GCT CAC GTG CCT CTC GGG TAG    1656
Thr Lys Glu Lys Leu Gln Arg Glu Ala His Val Pro Leu Gly End     552
```

*Figure 5C*

```
h  MKVLLRLICFIA-LLISSLEADKCKEREEKIILVSSANEIDVRPCPLNPNE--HKG-TITVYKDDSKTPVSTEQASRIHQHKEKLVFVPAK
   ||||| ||  ||  ||    |||| ||     |  |||| ||||  ||    |||   | |||||||||||| ||||| ||| |||||||
m  MKVLLGLICLMVPLL---SLEIDVCTEYPNQIVLFLSVNEIDIRKCPLTPNKMH-GDTIIVYKNDSKTPISADRDSRIHQQNEHLVFVPAK
                     *                            *                 △ h  VEDSGHYYCVVRNSSYCLRIKISAKFVENEPNLCYNAQAIFKQKLPVAGDGLVCPYHEFFKNENNELPKLQVYKDCKPLLLDNIHFSGV
   ||||| || ||||||||||| ||  |||||||| ||||  ||||||  |||| |||| | ||||||||||||| | |||||||  |||
m  VEDSGYYYCIVRNSTYCLKTKVTVTVLENDPGLCYSTQATPPQRLHIAGDGSLVCPYVSYFKDENNELPEVQVYKNCKPLLLDNVSFFGV
           △ *                                                * h  KDRLIVMNVAEKHRGNYTCHASYTYLGKQYPITRVIEFITLEENKPTRPVIVSPANETHEVDLGSQIQLICNVTGQLSDIAYVKWNGSVI
   || |||  ||| ||| ||||   ||  |||| || |   |||| | |||| |  |  ||||  | |||||||  ||| ||| ||||  |
m  KDKLLVRNVAEEHRGDYICRMSYTFRGKQYPVTRVIQFITIDENKRDRPVILSPRNETIEADPGSMIQLICNVTGQFSDLVYVKWNGSEI
      △                                     △                 *  △ h  DEDDPVLGEDYYSVENPANKRRSTLITVLNISEIESRFYKHPFTCFAKNTHGIDAAYIQLIYPVTNFQKHMIGICVTLTVIIVCSVFIYK
        ||    | ||  |||||  |||||  || |       |  ||   | |||||||||  ||| ||||| ||   |     | |||
m  EWNDPFLAEDYQFVEHPSTKRKYTLITTLNISEVKSQFYRYPFICVVKNTNIFESAHVQLIYPVPDFKNYLIGGPFILLTATIVCCVCIYK
                            △                          * h  IFKIDIVLVYRDSCYDFLPIKASDGKTYDAYILYPKTVGEGSTSDCDIFVFKVLPEVLEKQCGYKLFIYGRDDYVGEDIVEVINENVKKS
   || ||||| |||| |  ||| ||||||||||||||||  || || | |||| ||||||   || ||||||||| |||| |||| ||||||
m  VFKVDIVLVYRDSCSGFLPSKASDGKTYDAYILYPKTLGEGSFSDLDTFVFKLLPEVLEGQFGYKLFIYGRDDYVGEDTIEVTNENVKKS
                     * h  RRLIIILVRETSGFSVLGGSSEEQIAMYNALVQDGIKVVLLELEKIQDYEKMPESIKFIKQKH---------AKTRFVKNVRYH
   |||||||||  ||||||| |||||||||||| |||| ||||||||||||||||| | |||||          ||||||||  |
m  RRLIIILVRDMGGFSVLGQSSEEQIAIYNALIQEGIKIVLLELEKIQDYEKMPDSIQFIKQKHGVICWSGDFQERPQSAKTRFVKNLRYQ h  MPVQRRSPSSKHQLLSPA-----TKEKLQREAHVPLG
   || |||||  ||  |  |      |||| |  ||||
m  MPAQRRSPLSKHRLLTLDPVRDTKEKLPAATHLPLG
```

*Figure 8*

INTERLEUKIN-1 RECEPTORS

CROSS-REFERENCE TO RELATED APPLICATION

This application is a continuation-in-part of U.S. Application Ser. No. 07/160,550, filed Feb. 25, 1988, U.S. Pat. No. 4,968,607 which is a continuation-in-part of U.S. Application Ser. No. 7/125,627, filed Nov. 25, 1987 now abandoned.

BACKGROUND OF THE INVENTION

The present invention relates generally to cytokine receptors, and more specifically, to Interleukin-1 receptors.

Interleukin-1α and Interleukin-1β (IL-1α and IL-1β) are distantly related polypeptide hormones which play a central role in the regulation of immune and inflammatory responses. These two proteins were originally both classified as IL-1, based on a shared lymphocyte activation factor (LAF) activity, and a common major cellular source, activated macrophages. As information has accumulated from studies using purified natural and recombinant IL-1 molecules, it has become clear that IL-1α and IL-1β each mediate most, if not all, of the wide range of activities previously ascribed to IL-1. The basis for this nearly identical spectrum of biological activities is thought to be a single class of plasma membrane IL-1 receptors which bind both IL-1α and IL-1β.

A few preliminary reports concerning the existence of an IL-1 plasma membrane receptor have been published. To date, structural characterization of the Interleukin-1 receptor has been limited to estimates of the molecular weight of this protein by gel filtration, by SDS-PAGE analysis of covalent complexes formed by chemical crosslinking between the receptor and $^{125}$I-IL-1 molecules, and by immunoprecipitation of labeled surface proteins.

Dower et al. (*J. Exp. Med.* 162:501, 1985), and Dower et al. (*Proc. Natl. Acad. Sci. USA* 83:1060, 1986), describe chemical crosslinking studies indicating an apparent 79.5 kilodalton (kDa) plasma membrane protein on LBRM-33-1A5 murine T lymphoma cells and a 78 kDa surface protein on a murine fibroblast cell line which bound $^{125}$I-labeled human Interleukin-1β. Kilian et al. (*J. Immunol.* 136:4509, 1986) reported that murine $^{125}$I-IL-1α binding to murine thymoma cells could be blocked by human IL-1α and IL-1β. Dower et al. (*Nature* 324:266, 1986) reported binding competition studies indicating that IL-1α and IL-1β bound to the same cell surface receptors on LBRM-33-1A5 cells, human dermal fibroblasts, murine BALB-3T3 cells, and ARH77, a human B lymphoblastoid cell line. The receptors in the different cell lineages exhibited similar but not identical binding characteristics. The IL-1 receptors on porcine synovial fibroblasts (Bird et al., *Nature* 324:263, 1986) and human dermal fibroblasts (Chin et al., *J. Exp. Med.* 165:70, 1987) have been shown to yield a major species in the size range $M_r$97,000-100,000 when crosslinked to labeled IL-1, suggesting that a protein of $M_r$80,000 was responsible for binding IL-1. In contrast, IL-1 receptors characterized in this fashion on human B cells (Matsushima et al., *J. Immunol.* 136:4496, 1986) displayed an apparent molecular weight of 60,000.

Bron and MacDonald, *FEBS Letters* 219:365 (1987), disclose immunoprecipitation of murine IL-1 receptor from surface-labeled EL-4 cells using a rabbit polyclonal antiserum directed to IL-1. This work indicated that the murine receptor is a glycoprotein having an apparent molecular weight of approximately 82,000 daltons.

Radiolabeled IL-1 has been used in chemical crosslinking studies and for the detection of receptor in detergent extracts of cells. The results of these experiments, noted above, suggest that a protein of $M_r$ 60,000 or 80,000 is responsible for binding IL-1. The crosslinking of radiolabeled IL-1 to cells has also led to the occasional detection of proteins distinct from the major species of $M_r$ 80,000, suggesting that the IL-1 binding molecule may exist in the membrane as part of a multi-subunit receptor complex.

In order to study the structure and biological characteristics of IL-1 receptors and the role played by IL-1 receptors in the responses of various cell populations to IL-1 stimulation, or to use IL-1 receptors effectively in therapy, diagnosis, or assay, homogeneous compositions of IL-1 receptor are needed. Such compositions are theoretically available via purification of solubilized receptors expressed by cultured cells, or by cloning and expression of genes encoding the receptors. However, prior to the present invention, several obstacles prevented these goals from being achieved.

Even in cell lines known to express detectable levels of IL-1 receptor, the IL-1 receptor is present as a very minor component of total cellular proteins. Moreover, no cell lines were known that expressed high levels of IL-1 receptors constitutively and continuously. For example, the murine EL-4 6.1 cell line expresses detectable levels of IL-1 receptor, but the level of IL-1 receptor expression tends to decay with time, which greatly complicates the process of obtaining sufficient quantities of receptor to provide a useful starting material for purification. Thus, a method of continuously selecting cells for acceptable levels of IL-1 receptor expression, employing fluorescence-activated cell sorting (FACS), was devised.

Additional problems are inherent in attempting to clone mammalian genes encoding IL-1 receptor. Even if a protein composition of sufficient purity can be obtained to permit N-terminal protein sequencing, the degeneracy of the genetic code typically does not permit one to define a suitable probe without considerable additional experimentation. Many iterative attempts may be required to define a probe having the requisite specificity to identify a hybridizing sequence in a cDNA library. To circumvent this problem, a novel direct receptor expression cloning technique was devised to avoid the need for repetitive screening using different probes of unknown specificity. This technique, which has never before been employed, allows direct visualization of receptor expression following transfection of a mammalian cell line with a high expression vector containing a cDNA clone encoding the receptor.

Purified IL-1 receptor compositions will be useful in diagnostic assays for IL-1 or IL-1 receptor, and also in raising antibodies to IL-1 receptor for use in diagnosis or therapy. In addition, purified IL-1 receptor compositions may be used directly in therapy to bind or scavenge IL-1, thereby providing a means for regulating the immune or inflammatory activities of this cytokine.

SUMMARY OF THE INVENTION

The present invention provides DNA sequences consisting essentially of a single open reading frame nucleotide sequence encoding a mammalian Interleukin-1 receptor (IL-1R) or subunit thereof. Preferably, such DNA sequences are selected from the group consisting of (a) cDNA clones having a nucleotide sequence derived from the coding region of a native IL-1R gene; (b) DNA sequences capable of hybridization to the cDNA clones of (a) under moderately stringent conditions and which encode biologically active IL-1R molecules; and (c) DNA sequences which are degenerate as a result of the genetic code to the DNA sequences defined in (a) and (b) and which encode biologically active IL-1R molecules. The present invention also provides recombinant expression vectors comprising the DNA sequences defined above, recombinant IL-1R molecules produced using the recombinant expression vectors, and processes for producing the recombinant IL-1R molecules utilizing the expression vectors.

The present invention also provides substantially homogeneous protein compositions comprising murine or human IL-1 receptor. The murine molecule is a glycoprotein having a molecular weight of about 82,000 daltons by SDS-PAGE, a binding affinity ($K_a$) for human IL-1α of from $3-6 \times 10^9$ M$^{-1}$, and the N-terminal amino acid sequence L E I D V C T E Y P N Q I V L F L S V N E I D I R K.

In another aspect, the present invention provides a process for purifying IL-1 receptor, comprising applying a sample comprising IL-1 receptor to an affinity matrix comprising an IL-1 molecule bound to an insoluble support, and eluting bound IL-1 receptor from the affinity matrix. The partially purified IL-1 receptor can be further purified by application to a lectin affinity column and subsequently eluting the IL-1 receptor from the lectin affinity column. The partially purified IL-1 receptor can then be treated by reversed phase high performance liquid chromatography, and eluted as a single peak of absorbance at 280 nanometers which, when analyzed by SDS-PAGE and silver staining, appeared as a single band. As noted above, the native murine IL-1 receptor had an apparent molecular weight of approximately 82,000 daltons as estimated by SDS-PAGE.

The present invention also provides compositions for use in therapy, diagnosis, assay of IL-1 receptor, or in raising antibodies to IL-1 receptors, comprising effective quantities of soluble native or recombinant receptor proteins prepared according to the foregoing processes. Such soluble recombinant receptor molecules include truncated proteins wherein regions of the receptor molecule not required for IL-1 binding have been deleted. These and other aspects of the present invention will become evident upon reference to the following detailed description and attached drawings.

BRIEF DESCRIPTION OF THE DRAWINGS

FIG. 2 depicts the cDNA sequence of clone GEMBL78. Nucleotides are numbered from the beginning of the fragment. The CTG codon specifying the leucine residue constituting the N-terminus is underlined at position 282, and the TAG terminator codon which ends the open reading frame is underlined at position 1953.

FIGS. 3A-3C depict the cDNA sequence and derived amino acid sequence of the coding region of the cDNA shown in FIG. 2. In FIGS. 3A-3C, nucleotides and amino acids are numbered from the leucine residue representing the N-terminus of the mature protein. In FIGS. 3A-3C, the alternative initiator methionines, N-terminus, and 21 amino acid putative transmembrane region of the murine IL-1 receptor are underlined.

FIG. 4 depicts a cDNA sequence which includes the complete coding region of the human IL-1R gene. Nucleotides are numbered from the beginning of a fragment, designated R3A, which includes the N-terminus and a short sequence of 5' nontranslated DNA. The CTG codon specifying the leucine residue constituting the N-terminus is underlined at position 135, and the TAG terminator codon which ends the open reading frame is underlined at position 1791.

FIGS. 5A-5C depict the cDNA sequence and derived amino acid sequence of the coding region of a cDNA encoding human IL-1 receptor. In FIGS. 5A-5C, nucleotides and amino acids are numbered from the leucine residue (underlined) representing the N-terminus of the mature protein. The 20-amino acid transmembrane region is also underlined.

FIG. 7 provides a graphical comparison of the IL-1 binding characteristics of natural and recombinant IL-1 receptors. In FIG. 7, C indicates the concentration of IL-1 added to the binding incubation (molar); r indicates molecules of IL-1 bound per cell.

FIG. 8 is a comparison of the derived amino acid sequences of the murine and human IL-1 receptors. The transmembrane regions of each protein are underlined, and conserved cysteine residues are indicated by asterisks. Potential N-linked glycosylation sites are indicated by triangles adjacent to asparagine residues.

DETAILED DESCRIPTION OF THE INVENTION

Figure 1:
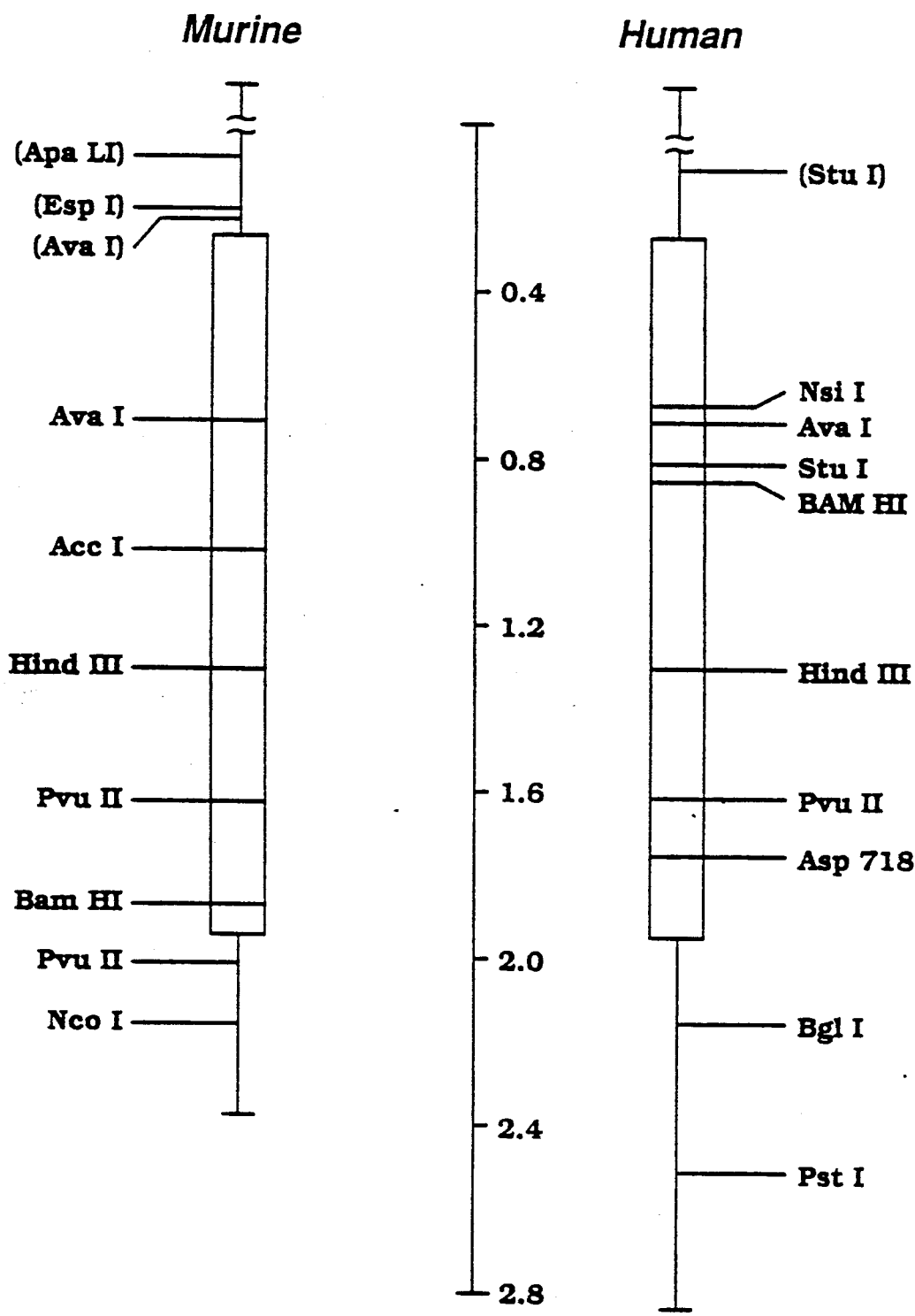
FIG. 1 is a restriction map of cDNA constructs comprising the coding regions of the murine and human IL-1R genes. The murine fragment, isolated from EL-4 6.1 C10 cells and present as an insert in clone GEMBL78, has been deposited with the American Type Culture Collection under deposit accession number ATCC 67563.

IL-1α and IL-1β apparently regulate the metabolism of cells through a common plasma membrane receptor protein. IL-1 receptor from detergent solutions of EL-4 6.1 C10 cells has been stably adsorbed to nitrocellulose with full retention of IL-1 binding activity. This assay system was used to monitor the purification of the IL-1 receptor and to investigate the effects of several chemical modifications on receptor binding activity. IL-1 receptors extracted from EL-4 6.1 C10 cells can be bound to and specifically eluted from IL-1α coupled to Sepharose or other suitable affinity chromatography supports.

Purification by the foregoing process resulted in the identification by silver staining of polyacrylamide gels of a protein of $M_r$ 82,000 daltons that was present in fractions exhibiting IL-1 binding activity. Experiments in which the cell surface proteins of EL-4 cells were radiolabeled and $^{125}$I labeled receptor was purified by affinity chromatography suggested that the $M_r$ 82,000 protein was expressed on the plasma membrane. N-glycanase treatment of this material showed that 21–35% of the total $M_r$ (82,000) of the receptor was N-linked carbohydrate.

In order to define the chemical properties of the IL-1 receptor, a simple, reproducible and quantitative assay system was devised for the detection of IL-1 receptor in detergent solutions. With this assay, receptor purification can be followed, and changes in receptor binding activity in response to chemical modification of the receptor can be easily monitored.

Binding Assay for IL-1 Receptor

Recombinant human IL-1β and IL-1α can be prepared by expression in *E. coli* and purification to homogeneity as described by Kronheim et al. (*Bio/Technology* 4:1078, 1986). Recombinant human IL-1α is preferably expressed as a polypeptide composed of the C-terminal 157 residues of IL-1α, which corresponds to the $M_r$ 17,500 form of the protein released by activated macrophages. The purified protein is stored at −70° C. in phosphate buffered saline as a stock solution of 3 mg/ml. 10 μl (30 μg) aliquots of the stock solution are labeled with sodium ($^{125}$I) iodide by a modified chloramine-T method described by Dower et al. (*Nature* 324:266, 1986) and Segal et al. (*J. Immunol.* 118:1338, 1977). In this procedure, 10 μg rIL-1α (0.57 nmol) in 10 μl phosphate (0.05M) buffered saline (0.15M) pH 7.2 (PBS) are added to 2.5 mCi (1.0 nmol) of sodium iodide in 25 μl of 0.05M sodium phosphate pH 7.0. The reaction is initiated by addition of 30 μl of $1.4 \times 10^{-4}$M chloramine-T (4.2 nmol; Sigma Chemical Co., St. Louis, MO., USA). After 30 minutes on ice the reaction mixture is fractionated by gel filtration on a 1 mL bed volume Biogel P6 (Bio-Rad, Richmond, CA., USA) column. Routinely, 40–50% of $^{125}$I is incorporated into protein.

$^{125}$I-IL-1α can be purified by gel filtration or other suitable methods and immediately diluted to a working stock solution of $3 \times 10^{-8}$M in Roswell Park Memorial Institute (RPMI) 1640 medium comprising 1% (w/v) bovine serum albumin (BSA), 0.1% (w/v) sodium azide, 20 mM Hepes pH 7.4 (binding medium), to avoid radiolysis. Such dilute solutions can be stored for up to one month without detectable loss of receptor binding activity. The specific activity is routinely in the range $1-3 \times 10^{15}$ cpm/mmole (ca 1 atom of iodine per IL-1α molecule). Typically, the labeled protein is initially (prior to dilution) 100% active as determined by its capacity to elicit IL-2 production from EL-4 6.1 C10 cells. Further, 100% of the $^{125}$I cpm can be precipitated by trichloroacetic acid and >95% can be absorbed by IL-1 receptor bearing cells.

EL-4 6.1 C10 cells are propagated in suspension culture as described by MacDonald et al., *J. Immunol.* 135:3964 (1985). An IL-1 receptor negative variant line of EL-4 cells, EL-4 (M) (ATCC TIB 39), is grown in an identical fashion. Cells are monitored on a weekly basis for IL-1 receptor expression by $^{125}$I-IL-1α binding.

To maintain relatively high levels of receptor expression, cells can be sorted using fluorescence-activated cell sorting (FACS) and fluorescein-conjugated recombinant IL-1α. Fluorescein-conjugated rIL-1α (FITC IL-1α) is prepared by reacting 2.9 nanomoles protein with 100 nanomoles of fluorescein isothiocyanate (Research Organics, Cleveland, Ohio) in a total volume of 70 μl of borate (0.02M) buffered saline (0.15M) pH 8.5 for two hours at 37° C. Protein is separated from unconjugated dye by gel filtration on a 1 ml bed volume P6 column, as described by Dower et al. (*J. Exp. Med.* 162:501, 1985). Using an EPICS C flow cytometer (Coulter Instruments; 488 nM argon laser line, 300 MW, gain 20, PMT voltage 1700), cells providing the highest level fluorescence signal (e.g., the top 1.0% or 0.1%, as desired) are collected and used to establish cell cultures for receptor expression.

For extractions, cells harvested from culture by centrifugation are washed once with binding medium and sedimented at 2000×g for 10 min to form a packed pellet (ca $8 \times 10^8$ cells/ml). To the pellet is added an equal volume of PBS containing 1% Triton X-100 and a cocktail of protease inhibitors (2 mM phenylmethylsulphonyl fluoride, 1 μM pepstatin, 1 μm leupeptin, and 2 mM 0-phenanthroline). The cells are mixed with the extraction buffer by vigorous vortexing and the mixture incubated on ice for 15 minutes; at the end of this time the mixture is centrifuged at 11,000×g for 30 minutes at 8° C. to remove nuclei and other debris. The supernatant is made 0.02% w/v in sodium azide and stored either at 8° C. or −70° C., with no loss in IL-1 receptor activity detected for periods of up to six months at either temperature.

For solid phase binding assays, unless otherwise indicated, 1 μl ($4 \times 10^5$ cell equivalents) aliquots of extract are placed on dry BA85/21 nitrocellulose membranes (Schleicher & Schuell, Keene, N.H.) and the membranes kept at room temperature until dry. Dry membranes can be stored at room temperature until use. Under these conditions, receptor binding activity remains stable for up to two months. Prior to use, membranes are reconstituted by incubating for 30 minutes in Tris (0.05M) buffered saline (0.15M) pH 7.5 containing 3% w/v BSA to block nonspecific binding sites, washed twice with PBS (20 ml per filter), once with binding medium and cut while wet into 0.9×0.9 cm squares with the IL-1 receptor extract at the center. The squares are placed in 24 well trays (Costar, Cambridge, MA) and covered with 200 μl of binding medium containing $^{125}$I-IL-1α or $^{125}$I-IL-1α and unlabeled inhibitors. Trays are then placed on a nutator and incubated in a refrigerator (8° C.) for two hours. At the end of this time a 60 μl aliquot can be taken from each well for determination of unbound $^{125}$I-rIL-1α. Subsequently, the remaining solution is aspirated and discarded and the nitrocellulose filters washed by adding and aspirating sequentially 1 ml of binding medium and three times 1 ml of PBS to each well. The nitrocellulose squares are then removed and dried on filter paper. Subsequently, they are either placed on Kodak X-omat AR film for twelve hours at −70° C., or placed in 12×75 cm glass tubes and counted on a gamma counter.

DEFINITIONS

"Interleukin-1 receptor" and "IL-1R" refer to proteins which are capable of binding Interleukin-1 (IL-1) molecules and, in their native configuration as mammalian plasma membrane proteins, presumably play a role in transducing the signal provided by IL-1 to a cell. As used herein, the term includes analogs of native proteins with IL-1-binding or signal transducing activity. Specifically included are truncated or soluble forms of the IL-1 receptor protein not having a cytoplasmic and transmembrane region. The predicted molecular weight of the murine protein corresponding to the sequence of the mature protein depicted in FIGS. 3A–3B is 64,597 daltons, while the predicted weight of the precursor is 66,697 daltons. Both of these estimates are exclusive of any glycosylation. The predicted molecular weight of the human protein corresponding to the sequence of the mature protein depicted in FIGS. 5A–5C is 63,486 daltons, while the predicted weight of the precursor is 65,402 daltons.

"Substantially identical" and "substantially similar," when used to define amino acid sequences, mean that a particular subject sequence, for example, a mutant sequence, varies from a reference sequence by one or more substitutions, deletions, or additions, the net effect of which does not result in an adverse functional dissimilarity between reference and subject sequences. For purposes of the present invention, amino acid sequences having greater than 30 percent similarity are considered to be substantially similar, and amino acid sequences having greater than 80 percent similarity are considered to be substantially identical. In defining nucleic acid sequences, all subject nucleic acid sequences capable of encoding substantially similar amino acid sequences are considered substantially similar to a reference nucleic acid sequence, and all nucleic acid sequences capable of encoding substantially identical amino acid sequences are considered substantially identical to a reference sequence. For purposes of determining similarity, truncation or internal deletions of the reference sequence should be disregarded. Sequences having lesser degrees of similarity, comparable biological activity, and equivalent expression characteristics are considered to be equivalents. For purposes of the present invention, a "subunit" of an IL-1R is deemed to constitute an amino acid sequence of at least 20 amino acids.

"Recombinant," as used herein, means that a protein is derived from recombinant (e.g., microbial or mammalian) expression systems. "Microbial" refers to recombinant proteins made in bacterial or fungal (e.g., yeast) expression systems. As a product, "recombinant microbial" defines a protein essentially free of native endogenous substances and unaccompanied by associated native glycosylation. Protein expressed in most bacterial cultures, e.g., E. coli, will be free of glycan; protein expressed in yeast may have a glycosylation pattern different from that expressed in mammalian cells.

"Biologically active," as used throughout the specification as a characteristic of IL-1 receptors, means either that a particular molecule shares sufficient amino acid sequence similarity with the embodiments of the present invention disclosed herein to be capable of binding at least 0.01 nmoles IL-1 per nanomole IL-1 receptor or IL-1 receptor analog, or, in the alternative, shares sufficient amino acid sequence similarity to be capable of transmitting an IL-1 stimulus to a cell, for example, as a component of a hybrid receptor construct. Preferably, biologically active IL-1 receptors within the scope of the present invention are capable of binding greater than 0.1 nanomoles IL-1 per nanomole receptor, and most preferably, greater than 0.5 nanomoles IL-1 per nanomole receptor.

"DNA sequence" refers to a DNA polymer, in the form of a separate fragment or as a component of a larger DNA construct, which has been derived from DNA isolated at least once in substantially pure form, i.e., free of contaminating endogenous materials and in a quantity or concentration enabling identification, manipulation, and recovery of the sequence and its component nucleotide sequences by standard biochemical methods, for example, using a cloning vector. Such sequences are preferably provided in the form of an open reading frame uninterrupted by internal nontranslated sequences, or introns, which are typically present in eukaryotic genes. However, it will be evident that genomic DNA containing the relevant sequences could also be used. Sequences of non-translated DNA may be present 5' or 3' from the open reading frame, where the same do not interfere with manipulation or expression of the coding regions.

"Nucleotide sequence" refers to a heteropolymer of deoxyribonucleotides. DNA sequences encoding the proteins provided by this invention are assembled from cDNA fragments and short oligonucleotide linkers, or from a series of oligonucleotides, to provide a synthetic gene which is capable of being expressed in a recombinant transcriptional unit.

"Recombinant expression vector" refers to a plasmid comprising a transcriptional unit comprising an assembly of (1) a genetic element or elements having a regulatory role in gene expression, for example, promoters or enhancers, (2) a structural or coding sequence which is transcribed into mRNA and translated into protein, and (3) appropriate transcription and translation initiation and termination sequences. Structural elements intended for use in yeast expression systems preferably include a leader sequence enabling extracellular secretion of translated protein by a host cell. Alternatively, where recombinant protein is expressed without a leader or transport sequence, it may include an N-terminal methionine residue. This residue may optionally be subsequently cleaved from the expressed recombinant protein to provide a final product.

"Recombinant microbial expression system" means a substantially homogeneous monoculture of suitable host microorganisms, for example, bacteria such as E. coli or yeast such as S. cerevisiae, which have stably integrated a recombinant transcriptional unit into chromosomal DNA or carry the recombinant transcriptional unit as a component of a resident plasmid. Generally, cells constituting the system are the progeny of a single ancestral transformant. Recombinant expression systems as defined herein will express heterologous protein upon induction of the regulatory elements linked to the DNA sequence or synthetic gene to be expressed.

Isolation of cDNAs Encoding IL-1 Receptors

In order to secure the murine coding sequence, a DNA sequence encoding murine IL-1R (mIL-1R) was isolated from a cDNA library prepared by reverse transcription of polyadenylated RNA isolated from the murine cell line EL-4 6.1 C10. The library was screened by direct expression of pooled cDNA fragments in monkey COS-7 cells using a mammalian expression vector (pDC201) that uses regulatory sequences derived from SV40 and Adenovirus 2. Transfectants expressing biologically active IL-1R were identified by incubating transfected COS-7 cells with medium containing $^{125}$I-IL-1$\alpha$, washing the cells to remove unbound labeled IL-1$\alpha$, and contacting the cell monolayers with X-ray film to detect concentrations of IL-1$\alpha$ binding. Transfectants detected in this manner appear as dark foci against a relatively light background.

Using this approach, approximately 150,000 cDNAs were screened in pools of approximately 350 cDNAs until assay of one transfectant pool indicated positive foci of IL-1$\alpha$ binding. A frozen stock of bacteria from this positive pool was grown in culture and plated to provide individual colonies, which were screened until a single clone (clone 78) was identified which directed synthesis of a surface protein with detectable IL-1 binding activity. This clone was isolated, and its insert sequenced to determine the sequence of the murine cDNA set forth in FIG. 2. The initiator methionine for the full-length translation product of the native murine gene is one of two alternative methionine residues found at positions -19 and -16 of FIG. 3A. The first amino acid residue of the mature receptor protein was deduced by comparison to an N-terminal amino acid sequence obtained from highly purified preparations of IL-1R derived from EL-4 6.1 C10 cells. This residue is a leucine residue shown at position 1 of FIG. 3A. The 1671 nucleotide coding region corresponding to the mature protein encodes 576 amino acids, including 15 cysteine residues and a 21-amino acid putative transmembrane region. Located N-terminal to the transmembrane region are 7 potential N-glycosylation sites. A cloning vector comprising the full-length murine cDNA, designated GEMBL78, has been deposited with the American Type Culture Collection, Rockville, MD., USA (ATCC) under accession number 67563. The deposit was made under the conditions of the Budapest Treaty.

A probe was constructed from the murine sequence and used to screen human cDNA libraries prepared from cultures of a human T-cell clone grown in the presence of OKT3 antibody and IL-2. cDNA clones which hybridized to the murine probe were then isolated and sequenced. Using a fragment derived from human cDNA clones, a 1707 nucleotide human coding sequence was obtained and sequenced. The nucleotide sequence of the human cDNA, including 5' and 3' non-translated sequences, is shown in FIG. 4. The nucleotide sequence of the human open reading frame and derived amino acid sequence of the human protein is set forth in FIGS. 5A-5C. This sequence comprises 569 amino acids (including a 17 amino acid signal peptide), including 16 cysteine residues, 13 of which are conserved between the murine and human genes. In addition, the human sequence includes six potential N-glycosylation sites, of which 5 are conserved between murine and human. The amino acid sequence of FIGS. 5A-5C is numbered from a leucine residue considered to be the likely N-terminus on the basis of comparison to the murine protein. The putative transmembrane region of the human gene is 20 amino acids in length. The sequences of the presumed intracellular portions of the murine and human genes are highly (87%) conserved; the extracellular (78%) and transmembrane regions (63%) are somewhat less conserved, except for the location of cysteines presumably involved in intramolecular disulfide bonding and certain N-glycosylation sites. The derived amino acid sequences of the human and murine genes are compared in FIG. 8.

The murine and human genes encode integral membrane proteins including intracellular regions having no apparent homology with any known protein sequence and extracellular portions which appear to be organized into domains similar to those of members of the immunoglobulin gene superfamily. Immunoglobulin-like domains typically possess only minimal amino acid similarity but share a common threedimensional structure consisting of two β-sheets held together by a disulfide bond. The cysteine residues involved in formation of this disulfide bond, as well as a few other critical residues, are highly conserved and occur in the same relative position in almost all members of the family. Members of the immunoglobulin superfamily include not only immunoglobulin constant and variable regions but also a number of other cell surface molecules, many of which are involved in cell-cell interactions.

Like most mammalian genes, mammalian IL-1Rs are presumably encoded by multi-exon genes. Alternative mRNA constructs which can be attributed to different mRNA splicing events following transcription, and which share large regions of identity or similarity with the cDNAs claimed herein, are considered to be within the scope of the present invention.

In its nucleic acid embodiments, the present invention provides DNA sequences encoding mammalian IL-1Rs. Examples of mammalian IL-1Rs include primate IL-1R, human IL-1R, murine, canine, feline, bovine, ovine, equine and porcine IL-1Rs. IL-1R DNAs are preferably provided in a form which is capable of being expressed in a recombinant transcriptional unit under the control of mammalian, microbial, or viral transcriptional or translational control elements. For example, a sequence to be expressed in a microorganism will contain no introns. In preferred aspects, the DNA sequences comprise at least one, but optionally more than one sequence component derived from a cDNA sequence or copy thereof. Such sequences may be linked or flanked by DNA sequences prepared by assembly of synthetic oligonucleotides. However, synthetic genes assembled exclusively from oligonucleotides could be constructed using the sequence information provided herein. Exemplary sequences include those substantially identical to the nucleotide sequences depicted in FIGS. 3A-3C. Alternatively, the coding sequences may include codons encoding one or more additional amino acids located at the N-terminus, for example, an N-terminal ATG codon specifying methionine linked in reading frame with the nucleotide sequence. Due to code degeneracy, there can be considerable variation in nucleotide sequences encoding the same amino acid sequence; exemplary DNA embodiments are those corresponding to the sequence of nucleotides 1-1671 of FIGS. 3A-3C, and nucleotides 1-1656 of FIGS. 5A-5C. Other embodiments include sequences capable of hybridizing to the sequence of FIGS. 3A-3C or 5A-5C under moderately stringent conditions (50° C., 2×SSC) and other sequences degenerate to those described above which encode biologically active IL-1R polypeptides.

The present invention also provides expression vectors for producing useful quantities of purified IL-1R. The vectors can comprise synthetic or cDNA-derived DNA fragments encoding mammalian IL-1Rs or bioequivalent homologues operably linked to regulatory elements derived from mammalian, bacterial, yeast, bacteriophage, or viral genes. Useful regulatory elements are described in greater detail below. Following transformation, transfection or infection of appropriate cell lines, such vectors can be induced to express recombinant protein.

Mammalian IL-1Rs can be expressed in mammalian cells, yeast, bacteria, or other cells under the control of appropriate promoters. Cell-free translation systems could also be employed to produce mammalian IL-1R using RNAs derived from the DNA constructs of the present invention. Appropriate cloning and expression vectors for use with bacterial, fungal, yeast, and mammalian cellular hosts are described by Pouwels et al. (*Cloning Vectors: A Laboratory Manual*, Elsevier, N.Y., 1985), the relevant disclosure of which is hereby incorporated by reference.

Various mammalian cell culture systems can be employed to express recombinant protein. Examples of suitable mammalian host cell lines include the COS-7 lines of monkey kidney cells, described by Gluzman (*Cell* 23:175, 1981), and other cell lines capable of expressing an appropriate vector, for example, the C127, 3T3, CHO, HeLa and BHK cell lines. Mammalian expression vectors may comprise nontranscribed elements such as an origin of replication, a suitable promoter and enhancer, and other 5' or 3' flanking nontranscribed sequences, and 5' or 3' nontranslated sequences, such as necessary ribosome binding sites, a polyadenylation site, splice donor and acceptor sites, and termination sequences. DNA sequences derived from the SV40 viral genome, for example, SV40 origin, early promoter, enhancer, splice, and polyadenylation sites may be used to provide the other genetic elements required for expression of a heterologous DNA sequence. Additional details regarding the use of a mammalian high expression vector to produce a recombinant mammalian IL-1R are provided in Examples 4 and 6, below. Exemplary vectors can be constructed as disclosed by Okayama and Berg (*Mol. Cell. Biol.* 3:280, 1983).

A useful system for stable high level expression of mammalian receptor cDNAs in C127 murine mammary epithelial cells can be constructed substantially as described by Cosman et al. (*Molecular Immunol.* 23:935, 1986).

Yeast systems, preferably employing Saccharomyces species such as *S. cerevisiae*, can also be employed for expression of the recombinant proteins of this invention. Yeast of other genera, for example, Pichia or Kluyveromyces, have also been employed as production strains for recombinant proteins.

Generally, useful yeast vectors will include origins of replication and selectable markers permitting transformation of both yeast and *E. coli*, e.g., the ampicillin resistance gene of *E. coli* and *S. cerevisiae* TRP1 gene, and a promoter derived from a highly-expressed yeast gene to induce transcription of a downstream structural sequence. Such promoters can be derived from yeast transcriptional units encoding highly expressed genes such as 3-phosphoglycerate kinase (PGK), α-factor, acid phosphatase, or heat shock proteins, among others. The heterologous structural sequence is assembled in appropriate reading frame with translation initiation and termination sequences, and, preferably, a leader sequence capable of directing secretion of translated protein into the extracellular medium. Optionally, the heterologous sequence can encode a fusion protein including an N-terminal identification peptide (e.g., Asp-Tyr-Lys- (Asp)$_4$-Lys) or other sequence imparting desired characteristics, e.g., stabilization or simplified purification of expressed recombinant product.

Useful yeast vectors can be assembled using DNA sequences from pBR322 for selection and replication in *E. coli* (Amp$^r$ gene and origin of replication) and yeast DNA sequences including a glucose-repressible alcohol dehydrogenase 2 (ADH2) promoter. The ADH2 promoter has been described by Russell et al. (*J. Biol. Chem.* 258:2674, 1982), and Beier et al. (*Nature* 300:724, 1982). Such vectors may also include a yeast TRP1 gene as a selectable marker and the yeast 2μ origin of replication. A yeast leader sequence, for example, the α-factor leader which directs secretion of heterologous proteins from a yeast host, can be inserted between the promoter and the structural gene to be expressed (see Kurjan et al., U.S. Pat. No. 4,546,082; Kurjan et al., *Cell* 30:933 (1982); and Bitter et al., *Proc. Natl. Acad. Sci. USA* 81:5330, 1984). The leader sequence may be modified to contain, near its 3' end, one or more useful restriction sites to facilitate fusion of the leader sequence to foreign genes.

Suitable yeast transformation protocols are known to those skilled in the art; an exemplary technique is described by Hinnen et al. (*Proc. Natl. Acad. Sci. USA* 75:1929, 1978), selecting for Trp$^+$ transformants in a selective medium consisting of 0.67% yeast nitrogen base, 0.5% casamino acids, 2% glucose, 10 μg/ml adenine and 20 μg/ml uracil.

Host strains transformed by vectors comprising the ADH2 promoter may be grown for expression in a rich medium consisting of 1% yeast extract, 2% peptone, and 1% glucose supplemented with 80 μg/ml adenine and 80 μg/ml uracil. Derepression of the ADH2 promoter occurs upon exhaustion of medium glucose. Crude yeast supernatants are harvested by filtration and held at 4° C. prior to further purification.

Useful expression vectors for bacterial use are constructed by inserting a DNA sequence encoding mammalian IL-1R together with suitable translation initiation and termination signals in operable reading phase with a functional promoter. The vector will comprise one or more phenotypic selectable markers and an origin of replication to ensure amplification within the host. Suitable prokaryotic hosts for transformation include *E. coli*, *Bacillus subtilis*, *Salmonella typhimurium*, and various species within the genera Pseudomonas, Streptomyces, and Staphylococcus, although others may also be employed as a matter of choice.

Expression vectors are conveniently constructed by cleavage of cDNA clones at sites close to the codon encoding the N-terminal residue of the mature protein. Synthetic oligonucleotides can then be used to "add back" any deleted sections of the coding region and to provide a linking sequence for ligation of the coding fragment in appropriate reading frame in the expression vector, and optionally a codon specifying an initiator methionine.

As a representative but nonlimiting example, useful expression vectors for bacterial use can comprise a selectable marker and bacterial origin of replication derived from commercially available plasmids comprising genetic elements of the well known cloning vector pBR322 (ATCC 37017). Such commercial vectors include, for example, pKK223-3 (Pharmacia Fine Chemicals, Uppsala, Sweden) and pGEM1 (Promega Biotec, Madison, WI., USA). These pBR322 "backbone" sections are combined with an appropriate promoter and the structural sequence to be expressed.

A particularly useful bacterial expression system employs the phage λ P$_L$ promoter and cI857 thermolabile repressor. Plasmid vectors available from the American Type Culture Collection which incorporate derivatives of the λ P$_L$ promoter include plasmid pHUB2, resident in *E. coli* strain JMB9 (ATCC 37092) and pPLc28, resident in *E. coli* RR1 (ATCC 53082). Other useful promoters for expression in *E. coli* include the T7 RNA polymerase promoter described by Studier et al. (*J. Mol. Biol.* 189:113, 1986), the lacZ promoter described by Lauer (*J. Mol. Appl. Genet.* 1:139–147, 1981) and available as ATCC 37121, and the tac promoter described by Maniatis (*Molecular Cloning: A Laboratory Manual*, Cold Spring Harbor Laboratory, 1982, p 412) and available as ATCC 37138.

Following transformation of a suitable host strain and growth of the host strain to an appropriate cell density, the selected promoter is derepressed by appropriate means (e.g., temperature shift or chemical induction) and cells cultured for an additional period. Cells are typically harvested by centrifugation, disrupted by physical or chemical means, and the resulting crude extract retained for further purification. Cells are grown, for example, in a 10 liter fermenter employing conditions of maximum aeration and vigorous agitation. An antifoaming agent (Antifoam A) is preferably employed. Cultures are grown at 30° C. in the superinduction medium disclosed by Mott et al. (*Proc. Natl. Acad. Sci. USA* 82:88, 1985), alternatively including antibiotics, derepressed at a cell density corresponding to $A_{600}=0.4-0.5$ by elevating the temperature to 42° C., and harvested from 2-20, preferably 3-6, hours after the upward temperature shift. The cell mass is initially concentrated by filtration or other means, then centrifuged at $10,000 \times g$ for 10 minutes at 4° C. followed by rapidly freezing the cell pellet.

Preferably, purified mammalian IL-1Rs or bioequivalent homologues are prepared by culturing suitable host/vector systems to express the recombinant translation products of the synthetic genes of the present invention, which are then purified from culture media.

An alternative process for producing purified IL-1R involves purification from cell culture supernatants or extracts. In this approach, a cell line which elaborates useful quantities of the protein is employed. Supernatants from such cell lines can be optionally concentrated using a commercially available protein concentration filter, for example, an Amicon or Millipore Pellicon ultrafiltration unit. Following the concentration step, the concentrate can be applied to a suitable purification matrix as previously described. For example, a suitable affinity matrix can comprise an IL-1 or lectin or antibody molecule bound to a suitable support. Alternatively, an anion exchange resin can be employed, for example, a matrix or substrate having pendant diethylaminoethyl (DEAE) groups. The matrices can be acrylamide, agarose, dextran, cellulose or other types commonly employed in protein purification. Alternatively, a cation exchange step can be employed. Suitable cation exchangers include various insoluble matrices comprising sulfopropyl or carboxymethyl groups. Sulfopropyl groups are preferred.

Finally, one or more reversed-phase high performance liquid chromatography (RP-HPLC) steps employing hydrophobic RP-HPLC media, e.g., silica gel having pendant methyl or other aliphatic groups, can be employed to further purify an IL-1R composition. Some or all of the foregoing purification steps, in various combinations, can also be employed to provide a homogeneous recombinant protein.

Recombinant protein produced in bacterial culture is usually isolated by initial extraction from cell pellets, followed by one or more concentration, salting-out, aqueous ion exchange or size exclusion chromatography steps. Finally, high performance liquid chromatography (HPLC) can be employed for final purification steps. Microbial cells employed in expression of recombinant mammalian IL-1R can be disrupted by any convenient method, including freeze-thaw cycling, sonication, mechanical disruption, or use of cell lysing agents.

Fermentation of yeast which express mammalian IL-1R as a secreted protein greatly simplifies purification. Secreted recombinant protein resulting from a large-scale fermentation can be purified by methods analogous to those disclosed by Urdal et al. (*J. Chromatog.* 296:171, 1984). This reference describes two sequential, reversed-phase HPLC steps for purification of recombinant human GM-CSF on a preparative HPLC column.

In its various embodiments, the present invention provides substantially homogeneous recombinant mammalian IL-1R polypeptides free of contaminating endogenous materials, with or without associated native-pattern glycosylation. The native murine IL-1R molecule is recovered from cell culture extracts as a glycoprotein having an apparent molecular weight by SDS-PAGE of about 82 kilodaltons (kD). IL-1Rs expressed in mammalian expression systems, e.g., COS-7 cells, may be similar or slightly different in molecular weight and glycosylation pattern to the native molecules, depending upon the expression system. Expression of IL-1R DNAs in bacteria such as E. coli provides non-glycosylated molecules having an apparent molecular weight of about 60 kD by SDS-PAGE under nonreducing conditions.

Recombinant IL-1R proteins within the scope of the present invention also include N-terminal methionyl murine and human IL-1Rs. Additional embodiments include soluble truncated versions wherein certain regions, for example, the transmembrane region and intracellular domains, are deleted, providing a molecule having an IL-1-binding domain only. Also contemplated are mammalian IL-1Rs expressed as fusion proteins with a polypeptide leader comprising the sequence Asp-Tyr-Lys-(Asp$_4$)-Lys, or with other suitable peptide or protein sequences employed as aids to expression in microorganisms or purification of microbially-expressed proteins.

Bioequivalent homologues of the proteins of this invention include various analogs, for example, truncated versions of IL-1Rs wherein terminal or internal residues or sequences not needed for biological activity are deleted. Other analogs contemplated herein are those in which one or more cysteine residues have been deleted or replaced with other amino acids, for example, neutral amino acids. Other approaches to mutagenesis involve modification of adjacent dibasic amino acid residues to enhance expression in yeast systems in which KEX2 protease activity is present, or modification of the protein sequence to eliminate one or more N-linked glycosylation sites.

As used herein, "mutant amino acid sequence" refers to a polypeptide encoded by a nucleotide sequence intentionally made variant from a native sequence. "Mutant protein" or "analog" means a protein comprising a mutant amino acid sequence. "Native sequence" refers to an amino acid or nucleic acid sequence which is identical to a wild-type or native form of a gene or protein. The terms "KEX2 protease recognition site" and "N-glycosylation site" are defined below. The term "inactivate," as used in defining particular aspects of the present invention, means to alter a selected KEX2 protease recognition site to retard or prevent cleavage by the KEX2 protease of *Saccharomyces cerevisiae*, or to alter an N-glycosylation site to preclude covalent bonding of oligosaccharide moieties to particular amino acid residues by the cell.

Site-specific mutagenesis procedures can be employed to inactivate KEX2 protease processing sites by deleting, adding, or substituting residues to alter Arg-Arg, Arg-Lys, and Lys-Arg pairs to eliminate the occurrence of these adjacent basic residues. Lys-Lys pairings are considerably less susceptible to KEX2 cleavage, and conversion of Arg-Lys or Lys-Arg to Lys-Lys represents a conservative and preferred approach to inactivating KEX2 sites. The resulting analogs are less susceptible to cleavage by the KEX2 protease at locations other than the yeast α-factor leader sequence, where cleavage upon secretion is intended.

Many secreted proteins acquire covalently attached carbohydrate units following translation, frequently in the form of oligosaccharide units linked to asparagine side chains by N-glycosidic bonds. Both the structure and number of oligosaccharide units attached to a particular secreted protein can be highly variable, resulting in a wide range of apparent molecular masses attributable to a single glycoprotein. mIL-1R is a glycoprotein of this type. Attempts to express glycoproteins in recombinant systems can be complicated by the heterogeneity attributable to this variable carbohydrate component. For example, purified mixtures of recombinant glycoproteins such as human or murine granulocyte-macrophage colony stimulating factor (GM-CSF) can consist of from 0 to 50% carbohydrate by weight. Miyajima et al. (*EMBO Journal* 5:1193, 1986) reported expression of a recombinant murine GM-CSF in which N-glycosylation sites had been mutated to preclude glycosylation and reduce heterogeneity of the yeast-expressed product.

The presence of variable quantities of associated carbohydrate in recombinant glycoproteins complicates purification procedures, thereby reducing yield. In addition, should the glycoprotein be employed as a therapeutic agent, a possibility exists that recipients will develop immune reactions to the yeast carbohydrate moieties, requiring therapy to be discontinued. For these reasons, biologically active, homogeneous analogs of immunoregulatory glycoproteins having reduced carbohydrate may be desirable for therapeutic use.

Functional mutant analogs of mammalian IL-1Rs having inactivated N-glycosylation sites can be produced by oligonucleotide synthesis and ligation or by site-specific mutagenesis techniques as described below. These analog proteins can be produced in a homogeneous, reduced-carbohydrate form in good yield using yeast expression systems. N-glycosylation sites in eukaryotic proteins are characterized by the amino acid triplet Asn-$A^1$-Z, where $A^1$ is any amino acid except Pro, and Z is Ser or Thr. In this sequence, asparagine provides a side chain amino group for covalent attachment of carbohydrate. Such a site can be eliminated by substituting another amino acid for Asn or for residue Z, deleting Asn or Z, or inserting a non-Z amino acid between $A^1$ and Z, or an amino acid other than Asn between Asn and $A^1$. Preferably, substitutions are made conservatively; i.e., the most preferred substitute amino acids are those having physicochemical characteristics resembling those of the residue to be replaced. Similarly, when a deletion or insertion strategy is adopted, the potential effect of the deletion or insertion upon biological activity should be considered.

In addition to the particular analogs described above, numerous DNA constructions including all or part of the nucleotide sequences depicted in FIGS. 3A-3C or 5A-5C, in conjunction with oligonucleotide cassettes comprising additional useful restriction sites, can be prepared as a matter of convenience. Mutations can be introduced at particular loci by synthesizing oligonucleotides containing a mutant sequence, flanked by restriction sites enabling ligation to fragments of the native sequence. Following ligation, the resulting reconstructed sequence encodes an analog having the desired amino acid insertion, substitution, or deletion.

Alternatively, oligonucleotide-directed site-specific mutagenesis procedures can be employed to provide an altered gene having particular codons altered according to the substitution, deletion, or insertion required. By way of example, Walder et al. (*Gene* 42:133, 1986); Bauer et al. (*Gene* 37:73, 1985); Craik (*Biotechniques*, January 1985, 12-19); Smith et al. (*Genetic Engineering: Principles and Methods*, Plenum Press, 1981); and U.S. Pat. No. 4,518,584 disclose suitable techniques, and are incorporated by reference herein.

In one embodiment of the present invention, the amino acid sequence of IL-1R is linked to a yeast α-factor leader sequence via an N-terminal fusion construct comprising a nucleotide encoding the peptide Asp-Tyr-Lys-Asp-Asp-Asp-Asp-Lys (DYKDDDDK). The latter sequence is highly antigenic and provides an epitope reversibly bound by specific monoclonal antibody, enabling rapid assay and facile purification of expressed recombinant protein. This sequence is also specifically cleaved by bovine mucosal enterokinase at the residue immediately following the Asp-Lys pairing. Fusion proteins capped with this peptide may also be resistant to intracellular degradation in *E. coli*. An alternative construction is Asp-Tyr-Lys-Asp-Asp-Asp-Asp-Lys-Glu-Ile-Gly-Arg, which provides a Factor X recognition site immediately downstream from the enterokinase site.

The following examples are offered by way of illustration, and not by way of limitation.

EXAMPLES

Example 1

Preparation of IL-1α Affinity Matrix and Affinity Purification of Receptor from Surface Labeled EL-4 6.1 C10 Cells Cell surface proteins on EL-4 6.1 C10 cells were radiolabeled with $^{125}I$ by the glucose oxidase-lactoperoxidase method disclosed by Cosman et al. (*Molecular Immunol.* 23:935, 1986). Labeled cells were pelleted by centrifugation, washed three times with PBS, and extracted with PBS containing 1% Triton X-100 and the cocktail of protease inhibitors described in the assay protocol detailed above. The Triton X-100 extract was spun for 10 minutes in an Eppendorf microcentrifuge and the supernatant was stored at −70° C.

Recombinant IL-1α was coupled to cyanogen bromide activated Sepharose 4B (Pharmacia, Piscataway, N.J., USA) or to Affigel-10 (Bio-Rad, Richmond, CA., USA) according to the manufacturer's suggestions. For example, to a solution of IL-1α (1.64 mg/ml in 9.5 ml PBS), 3 ml were added of swollen, acid-washed, CNBR-activated Sepharose. The solution was rocked overnight at 4° C. and an aliquot of the supernatant was tested for protein by a fluorescamine protein assay as described by Udenfried et al. (*Science* 178:871, 1972), using BSA as a standard. Ninety-eight percent of the protein had coupled to the gel, suggesting that the column had a final load of 5.1 mg IL-1α per ml gel. Three hundred μl of 1M glycine-ethyl-ester (Sigma Chemical Co., St. Louis, MO., USA) were added to the slurry to block any unreacted sites on the gel.

The gel was washed extensively with 0.1M glycine buffer pH 3.0 containing 0.1% Triton X-100, PBS containing 0.1% Triton X-100, RIPA buffer (0.05M Tris-HCl pH 7.5, 0.15M NaCl, 1% NP40, 1% sodium deoxycholate, 0.1% SDS), and PBS containing 0.1% Triton X-100 and 10 mM ATP. Small columns (200 μl) were prepared in disposable polypropylene holders (Bio-Rad, Richmond, CA., USA) and washed with PBS containing 1% Triton X-100. Aliquots of 100 μl of $^{125}$I-labeled extract were applied to a column, which was then washed with PBS containing 1% Triton X-100, RIPA buffer, PBS containing 0.1% Triton X-100 and 10 mM ATP, and PBS with 1% Triton X-100.

The IL-1 receptor on murine T cells is a robust structure capable of binding $^{125}$I-IL-1α in Triton X-100 detergent solutions. To be able to recover receptor from such an affinity matrix, a mild elution procedure is necessary. Mild acid treatment can cause rapid dissociation of preformed IL-1α/IL-1 receptor complexes. Based upon this observation, pH 3.0 glycine HCl buffer containing 0.1% Triton X-100 were used to elute receptor from the IL-1α affinity columns, which was collected in 0.05 ml fractions. The presence of receptor in the fractions was detected by dot blot as described above, using $^{125}$I-labeled IL-1α.

Analysis by SDS-PAGE proceeded as follows. To 50 μl of each column fraction was added 50 μl of 2×SDS sample buffer (0.125M Tris HCl pH 6.8, 4% SDS, 20% glycerol, 10% 2-mercaptoethanol). The solution was placed in a boiling water bath for three minutes and aliquots of 40 μl were applied to the sample well of a 10% polyacrylamide gel which was set up and run according to the method of Laemmli (*Nature* 227:680, 1970). Gels were fixed and stained using 0.25% Coomassie brilliant blue in 25% isopropanol, 10% acetic acid), destained in 25% isopropanol, 10% acetic acid, treated with Enhance (New England Nuclear, Boston, MA., USA), dried and exposed to Kodak X-omat AR film at −70° C. Molecular weight markers, labeled with $^{14}$C., were obtained from New England Nuclear, and included: cytochrome C ($M_r$ 12,300), lactoglobulin A ($M_r$ 18,367), carbonic anhydrase ($M_r$ 31,000), ovalbumin ($M_r$ 46,000), bovine serum albumin ($M_r$ 69,000), phosphorylase B ($M_r$ 97,400) and myosin ($M_r$ 200,000). Alternatively, fractions having receptor activity were analyzed by SDS polyacrylamide gel electrophoresis followed by silver staining as previously described by Urdal et al. (*Proc. Natl. Acad. Sci. USA* 81:6481, 1984).

Dot blot analysis of fractions eluted from the IL-1α affinity matrix showed that IL-1 binding activity was detected in fractions that were collected after pH 3.0 glycine buffer was applied to the column. Fractions that scored positive in this assay, when analyzed by SDS-PAGE, revealed that a protein of $M_r$ 82,000 could be detected upon developing the gel with silver stain. To determine which of the proteins detected by silver stain were expressed on the cell surface, EL-4 6.1 cells were surface labeled with $^{125}$I by the lactoperoxidaseglucose oxidase procedure. Radiolabeled cells were then extracted with PBS containing 1% Triton X-100 and aliquots of the detergent extract applied to an IL-1α affinity matrix. Fractions that were collected from this column, following application to the column of pH 3.0 glycine buffer, contained a radiolabeled protein of $M_r$ 82,000.

Example 2

Comparison of Properties of Cellular IL-1 Receptor and IL-1 Receptor Isolated from Cell Extracts In a preliminary experiment, the binding properties of the IL-1 receptor were compared in intact EL-4 6.1 C10 cells and after extraction from cells. $3.8 \times 10^8$ EL-4 6.1 C10 cells were divided into two equal aliquots, one of which was extracted as described above. The remaining cells were resuspended at $3.8 \times 10^7$ cells/ml and used for direct binding studies. Extract was adsorbed to nitrocellulose and used for solid phase binding studies employing various concentrations of $^{125}$I-IL-1α with or without unlabeled IL-1. After washing and drying, the nitrocellulose filters were first counted for bound $^{125}$I-IL-1α and subsequently placed on film for autoradiography. Nonspecific background was measured in the presence of $5.7 \times 10^{-7}$M unlabeled rIL-1β. The data obtained showed that $^{125}$I-IL-1α was bound to the extract on nitrocellulose in an IL-1 concentration-dependent fashion, and that the $^{125}$I-IL-1α was specifically bound to the region of the blot where extract is present. Further, binding could be extensively blocked by inclusion of unlabeled IL-1α in the incubation mixture.

The comparison further indicated that not only were the levels of receptor the same in both instances, but that the receptors after adsorption to nitrocellulose exhibited an affinity for ligand which was indistinguishable from that of the receptor in intact cells. No significant difference between the number of receptors detected on intact cells and those detected following detergent extraction was found. This is consistent with the view that the majority of the receptors were present on the external face of the plasma membrane in intact cells.

To measure the specificity of binding of IL-1 receptors on nitrocellulose filters, two μl of EL-4 6.1 C10 extract were applied to nitrocellulose filters, dried, blocked and assayed as described above. The following proteins were tested for their capacity to inhibit $^{125}$I-IL-1α binding: human rIL-1α ($7.62 \times 10^{-7}$M), human rIL-1β ($7.62 \times 10^{-7}$M), human IL-2 ($8.9 \times 10^{-7}$M), mureine IL-3 ($7.5 \times 10^{-4}$M), murine-GM-CSF ($7.5 \times 10^{-7}$M), recombinant murine IL-4 ($5 \times 10^{-9}$M), human epidermal growth factor 3 μg/ml, fibroblast growth factor 1 μg/ml, rat submandibular gland nerve growth factor (2 μg/ml), bovine insulin ($1 \times 10^{-7}$M), human luteinizing hormone (1 μg/ml), human growth hormone ($1.7 \times 10^{-7}$M), thyroid stimulating hormone (1 μg/ml), and follicle stimulating hormone (1 μg/ml). All incubations were done with $1.9 \times 10^{-10}$M $^{125}$I-IL-1α.

This experiment demonstrated that extracted receptor retains the same specificity as that previously demonstrated for intact cells. As found with intact cells, only IL-1α and IL-1β produced any significant inhibition of $^{125}$I-IL-1α binding. The data showed that unlabeled IL-1α and IL-1β produced >90% inhibition of $^{125}$I-IL-1α binding, while no significant blockade was observed with any of the other hormones.

To determine whether receptor in detergent solution would bind IL-1 with an affinity equal to that of receptor in cell membranes, or adsorbed to nitrocellulose, a third experiment was performed in which the nitrocellulose dot blot binding assay was used to test the capacity of an EL-4 6.1 C10 extract in Triton X-100 solution to inhibit binding of $^{125}$I-IL-1α to the solid phase. EL-4 6.1 C10 extracts were adsorbed to nitrocellulose, dried, blocked and incubated with mixture of $^{125}$I-IL-1α and extracts containing receptors in detergent solution.

The concentration of receptor in the solution phase was estimated from a saturation binding curve to 1 μl aliquots blotted on nitrocellulose, allowing receptors/μl to be calculated and hence IL-1 receptor concentration (M). The extract was diluted through PBS Triton X-100 solution (0.5% Triton) to keep the detergent concentration constant. The inhibition curve showed that in solution, the receptor bound to $^{125}$I-IL-1α with a $K_a$ ($4.5 \pm 0.5 \times 10^9 M^{-1}$) that is the same as that of receptor on the solid phase or in membranes. Further, the close fit between the theoretical curve, which is based on a simple competitive inhibition model, and the data was consistent with the hypothesis that a single type of IL-1 binding protein was present in the membrane extract.

In order to examine the integrity of the receptor as a function of the concentration of total EL-4 6.1 C10 membrane proteins, a fourth experiment was done. Mixtures of EL-4 6.1 C10 extract in various proportions ranging from 10 to 100% were made either with an extract from cells not expressing the IL-1 receptor, EL-4 (M) cells, or with PBS Triton X-100 (0.5%). Each mixture was analyzed for receptor concentration, and affinity of $^{125}$I-IL-1α binding by quantitative dot blot binding. Receptor concentration decreased linearly with the percentage of EL-4 6.1 C10 extract present, whether membrane protein concentration was maintained at a constant level or not. In both series of mixtures the affinity of the receptor for $^{125}$I-IL-1α remained constant. These data are consistent with one of two hypotheses, either the receptor binding function is contained within a single polypeptide chain or, if the functional receptor requires two or more subunits for IL-1 binding, these are sufficiently tightly associated that dilution through detergent does not separate them.

Example 3

Purification of IL-1 Receptor to Homogeneity and Determination of N-terminal Sequence 300–500 liters of EL-4 6.1 C10 cells were grown to saturation under the conditions previously described, harvested, and extracted with PBS-1% Triton X-100. The detergent extract was applied to an IL-1α affinity column and the column washed as previously described. Fractions containing IL-1 receptor were detected by the $^{125}$I-IL-1α dot blot procedure following elution of the column with 0.1M glycine HCl pH 3.0 containing 0.1% Triton X-100. Aliquots of the fractions were analyzed by SDS polyacrylamide gel electrophoresis.

This partially purified IL-1 receptor composition prepared by affinity chromatography on Affigel-IL-1α was adjusted to contain the following buffer composition: 10 mM Tris-HCl, pH 8, 250 mM NaCl, 0.5 mM $MgCl_2$, 0.5 mM $MnCl_2$, 0.5 mM $CaCl_2$, and 0.01% (v/v) Triton X-100 (WGA buffer). The IL-1 receptor composition was then applied to a 1 ml column of wheat germ agglutinin (WGA) bound to Sepharose CL-6 , equilibrated with WGA buffer. Following application of the IL-1 receptor composition, the WGA column was washed with 20 ml of WGA buffer followed by 10 mM Tris HCl, pH 8, 0.01% (v/v) Triton X-100. The IL-1 receptor protein was eluted from the WGA column with 10 mM Tris-HCl, pH 8, 0.5M N-acetylglucosamine, and 0.01% (v/v) Triton X-100. The presence of biologically active IL-1 receptor was detected by the $^{125}$I-IL-1α dot blot procedure. The fractions were also analyzed by SDS polyacrylamide gel electrophoresis followed by silver staining.

Material eluting from the WGA column was applied to a C8 RP-HPLC column. The C8 RP-HPLC column (Brownlee Labs RP-300, 1 mm × 50 mm) was previously equilibrated with 0.1% (v/v) trifluoroacetic acid (TFA) in HPLC grade $H_2O$, at a flow rate of 50 μl/min. Following application of the IL-1 receptor containing material, the C 8 RP-HPLC column was washed with 0.1% (v/v) TFA in $H_2O$ at 50 μl/min until the absorbance at 280 nm returned to baseline. The IL-1 receptor protein was eluted from the column by running a linear gradient of 0.1% (v/v) TFA in acetonitrile from 0–100% at a rate of 1% per minute. Aliquots of the fractions were analyzed by SDS polyacrylamide gel electrophoresis. The IL-1 receptor protein was found to consist of a single band on an SDS polyacrylamide gel migrating with a molecular weight of 82,000.

The purified IL-1 receptor protein was analyzed by Edman degradation using an Applied Biosystems Model 470 A protein sequencer. The protein (150 picomoles) was not modified before analysis. The results of the N-terminal protein sequence analysis of the IL-1 receptor indicated the following sequence of amino acid residues: $NH_2$-Leu-Glu-Ile-Asp-Val-Cys-Thr-Glu-Tyr-Pro-Asn-Gln-Ile-Val-Leu-Phe-Leu-Ser-Val-Asn-Glu-Ile-Asp-Ile-Arg-Lys.

This protein sequence was found to be unique when compared to the Mar. 17, 1987 release of the Protein Sequence Database of the Protein Identification Resource of the National Biomedical Research Foundation. This release of the database contained 4,253 sequences consisting of 1,029,056 residues.

Example 4

Isolation of cDNA Encoding Murine IL-1R by Direct Expression of Active Protein in COS-7 Cells A cDNA library was constructed by reverse transcription of polyadenylated mRNA isolated from total RNA extracted from EL-4 6.1 C10 cells by a procedure similar to that of Chirgwin et al. (*Biochem.* 18:5294, 1979). Briefly, the cells were lysed in a guanidinium isothiocyanate solution, and the lysate layered over a pad of CsCl and centrifuged until the RNA had pelleted. The RNA pellet was resuspended and further purified by protease digestion, organic extraction and alcohol precipitation. Poly $A^{30}$ RNA was isolated by oligo dT cellulose chromatography and double-stranded cDNA was prepared by a method similar to that of Gubler and Hoffman (*Gene* 25:263, 1983). Briefly, the RNA was copied into cDNA by reverse transcriptase using either oligo dT or random oligonucleotides as primer. The cDNA was made double-stranded by incubation with *E. coli* DNA polymerase I and RNase H, and the ends made flush by further incubation with $T_4$ DNA polymerase. The blunt-ended cDNA was ligated into SmaI-cut dephosphorylated pDC201 vector DNA.

The eukaryotic high expression vector pDC201 was assembled from SV40, adenovirus 2, and pBR322 DNA comprising, in sequence: (1) an SV40 fragment containing the origin of replication, early and late promoters, and enhancer; (2) an adenovirus 2 fragment containing the major late promoter, the first exon and part of the first intron of the tripartite late leader; (3) a synthetic sequence comprising a HindIII site, a splice acceptor site, the second and third exons of the adenovirus 2 tripartite leader and a multiple cloning site including a SmaI site; (4) additional SV40 sequences containing early and late polyadenylation sites; (5) adenovirus 2 sequences including the virus-associated RNA genes; and (6) pBR322 elements for replication in *E. coli*.

The resulting EL-4 6.1 C10 cDNA library in pDC201 was used to transform *E. coli* strain DH5α, and recombinants were plated to provide approximately 350 colonies per plate and sufficient plates to provide approximately 25,000 total colonies per screen. Colonies were scraped from each plate, pooled, and plasmid DNA prepared from each pool. The pooled DNA was then used to transfect a sub-confluent layer of monkey COS-7 cells using DEAE-dextran followed by chloroquine treatment, as described by Luthman et al. (*Nucleic Acids Res.* 11:1295, 1983) and McCutchan et al. (*J. Natl. Cancer Inst.* 41:351, 1986). The cells were then grown in culture for three days to permit transient expression of the inserted sequences. After three days, cell culture supernatants were discarded and the cell monolayers in each plate assayed for IL-1 binding as follows. Three ml of RPMI medium containing $3 \times 10^{-10}$M $^{125}$I-IL-1α was added to each plate and the plates incubated for 2 hours at 8° C. This medium was then discarded, and each plate was washed with 10 ml RPMI 1640 medium [containing no labeled IL-1α]. The edges of each plate were then broken off, leaving a flat disk which was contacted with X-ray film for 72 hours at $-70°$ C. using an intensifying screen. IL-1 binding activity was visualized on the exposed films as a dark focus against a relatively uniform background.

After approximately 150,000 recombinants from the library had been screened in this manner, one transfectant pool was observed to provide IL-1 binding foci which were clearly apparent against the background exposure.

A frozen stock of bacteria from the positive pool was then used to obtain plates of approximately 350 colonies. Replicas of these plates were made on nitrocellulose filters, and the plates were then scraped and plasmid DNA prepared and transfected as described above to identify a positive plate. Bacteria from individual colonies from the nitrocellulose replicas of this plate were grown in 2 ml cultures, which were used to obtain plasmid DNA, which was transfected into COS-7 cells as described above. In this manner, a single clone, clone 78, was isolated which was capable of inducing expression of IL-1R in COS cells. The insert was subcloned into a plasmid derived from pBR322 (GEMBL) and sequenced by conventional techniques. The sequence is set forth in FIG. 2.

Example 5

Isolation of Human cDNA Clones Which Hybridize to Murine IL-1 Receptor Probe DNAs A cDNA polynucleotide probe was prepared from the 2356 base pair (bp) fragment of clone 78 (see Example 4) by nick-translation using DNA polymerase I. The method employed was substantially similar to that disclosed by Maniatis et al. (supra, p. 109).

A cDNA library was constructed by reverse transcription of polyadenylated mRNA isolated from total RNA extracted from the cultured cells of a human T-cell line designated clone 22, described by Acres et al. (*J. Immunol.* 138:2132, 1987). These cells were cultured in RPMI 1640 medium plus 10% fetal bovine serum as described by Acres et al. (supra), in the presence of 10 ng/ml OKT3 antibody and 10 ng/ml human IL-2. The cDNA was rendered double-stranded using DNA polymerase I, blunt-ended with T4 DNA polymerase, methylated with EcoRI methylase to protect EcoRI cleavage sites within the cDNA, and ligated to EcoRI linkers. The resulting constructs were digested with EcoRI to remove all but one copy of the linkers at each end of the cDNA, and ligated to EcoRI-cut and dephosphorylated arms of bacteriophage λgt10 (Huynh et al., *DNA Cloning: A Practical Approach*, Glover, ed., IRL Press, pp. 49–78). The ligated DNA was packaged into phage particles using a commercially available kit (Stratagene Cloning Systems, San Diego, CA., USA 92121) to generate a library of recombinants. Recombinants were plated on *E. coli* strain C600(hfl$^-$) and screened by standard plaque hybridization techniques under conditions of moderate stringency (50° C., 6×SSC).

Following several rounds of screening, nine clones were isolated from the library which hybridized to the cDNA probe. The clones were plaque purified and used to prepare bacteriophage DNA which was digested with EcoRI. The digests were electrophoresed on an agarose gel, blotted onto nylon filters, and retested for hybridization. The clones were digested with EcoRI followed by preparative agarose gel electrophoresis, then subcloned into an EcoRI-cut derivative (pGEMBL) of the standard cloning vector pBR322 containing a polylinker having a unique EcoRI site, a BamH1 site and numerous other unique restriction sites. An exemplary vector of this type is described by Dente et al. (*Nucleic Acids Research* 11:1645, 1983).

Restriction mapping and sequencing of a 4.8 kb human IL-1R clone indicated that the clone included a sequence encoding 518 amino acids which exhibited 80% amino acid sequence identity to the corresponding murine sequence in the extracellular, or N-terminal region distal to the transmembrane region, 63% identity in the transmembrane region, and 87% identity in the cytoplasmic, or C-terminal region. In addition, several cysteine residues and most N-linked glycosylation sites between the mouse and human sequences were conserved. A 440 bp EcoRI-NsiI fragment derived from the 5' portion of the human IL-1R clone was $^{32}$P-labeled by nick-translation as described above and used to screen a cDNA library produced by randomly-priming clone 22 mRNA prepared as described above. 23 clones which hybridized to the probe were isolated and analyzed by restriction mapping. Sequencing of one of these clones provided the sequence information corresponding to the remaining N-terminal 34 amino acids of the human protein. The coding and deduced amino acid sequence of the complete coding region of human IL-1R is shown in FIGS. 5A–5C.

Example 6

Figure 6:
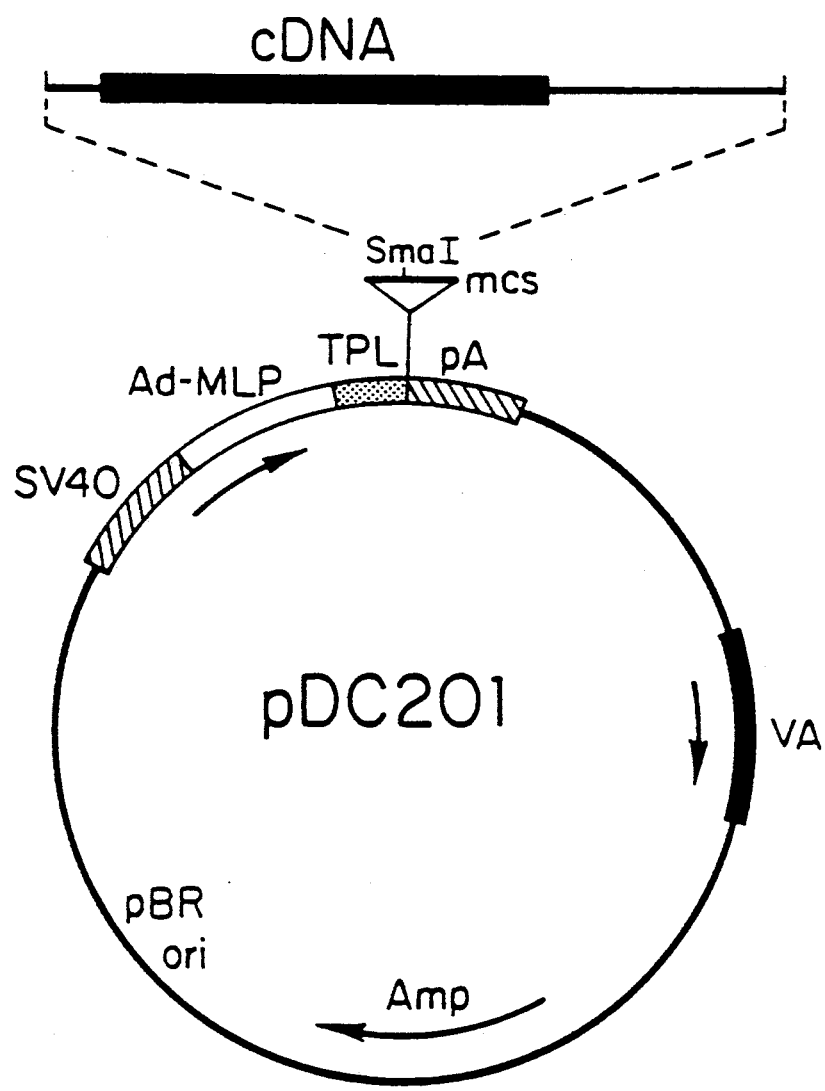
FIG. 6 is a schematic illustration of the mammalian high expression plasmid pDC201, which is described in greater detail in Example 6.

Expression of Recombinant IL-1 Receptor Using a High-Efficiency Mammalian Expression System The mammalian expression plasmid pDC201, depicted in FIG. 6, is designed to express cDNA sequences inserted at its multiple cloning site (MCS) when transfected into mammalian cells. Referring now to FIG. 6, pDC201 includes the following components: SV40 (hatched box) contains SV40 sequences from coordinates 5171-270 including the origin of replication, enhancer sequences and early and late promoters. The fragment is oriented so that the direction of transcription from the early promoter is as shown by the arrow. Ad-MLP (open box) contains adenovirus-2 sequences from coordinates 5779-6231 including the major late promoter, the first exon and part of the intron between the first and second exons of the tripartite leader. TPL (stippled box) contains a synthetic DNA sequence specifying adenovirus-2 sequences 7056-7172, 9634-9693 (containing the acceptor splice site of the second exon of the tripartite leader, the second exon and part of the third exon of the tripartite leader) and a multiple cloning site (MCS) containing sites for KpnI, SmaI, and BglII. pA (hatched box) contains SV40 sequences from 4127-4100 and 2770-2533 that include the polyadenylation and termination signals for early transcription. VA (solid box) contains adenovirus-2 sequences from 10226-11555 that include the virus-associated RNA genes (VAI and VAII). The solid lines are derived from pBR322 and represent (starting after the pA sequences and proceeding clockwise) coordinates 29-23, 651-185 (at which point the VA sequences are inserted), 29-1, 4363-2486, and 1094-375. pDC201 is a derivative of pMLSV, previously described by Cosman et al., *Molec. Immunol.* 23:935 (1986).

To express recombinant IL-1 receptor, COS cells were grown and transfected as described by Cosman et al., supra, with the plasmid DNA from a 1.5 ml culture of *E. coli* transformed with pDC201 having an IL-1R cDNA insert (clone 78). After 72 hours of culture cells were harvested by washing once with 10 ml of PBS and then treating for 20 minutes at 37° C. with an EDTA solution (sodium phosphate 0.05M, sodium chloride 0.15M, EDTA 0.005M, pH 7.4) followed by scraping. For comparisons, COS cells were transfected with a pDC201 control vector containing no insert, and EL-4 6.1 C10 cells and EL-4M cells (an IL-1 receptor-negative variant of EL-4 cells) were grown and harvested as described by McDonald et al., *J. Immunol.* 135:3964 (1985).

At saturating DNA concentrations, the transfected COS cell monolayer contained an average of 45,000 sites per cell. Since the parental COS cells expressed only about 500 receptors per cell, it can be calculated that more than 98% of all IL-1 receptors in the transfected population were recombinant. Flow cytometry using FITC-IL-1α revealed that only 4.2% of the cells stained brightly; therefore, each of these transfected COS cells contained about $1.1 \times 10^6$ IL-1 binding sites.

The plasma membrane proteins of EL-4 6.1 C10 cells and of COS cells transfected with vector DNA containing cDNA encoding the IL-1 receptor (clone 78) were labeled with $^{125}$I as described in Example 1, above. Cells were subsequently extracted with PBS containing 1% Triton X-100 and a cocktail of protease inhibitors (2 mM phenylmethyl sulphonyl fluoride, 1 mM pepstatin, 1 mM leupeptin, and 2 mM O-phenanthroline). Detergent extracts were subjected to affinity chromatography as described in Example 1 on Affigel-10 (Biorad, Richmond, CA.) to which recombinant human IL-1α had been coupled. $^{125}$I-labeled receptor was then eluted with sample buffer (0.0625M Tris-HCl pH 6.8, 2% SDS, 10% glycerol, 5% 2-mercaptoethanol) and analyzed by SDS polyacrylamide gel electrophoresis on a 10% gel. Gels were then subjected to autoradiography. The recombinant IL-1 receptor purified by affinity chromatography on IL-1α columns migrated with a relative mobility of about 80,000 on SDS polyacrylamide gels, comparable to the mobility displayed by IL-1 receptor purified in the same manner from EL-4 6.1 C10 cells.

Figure 7A:
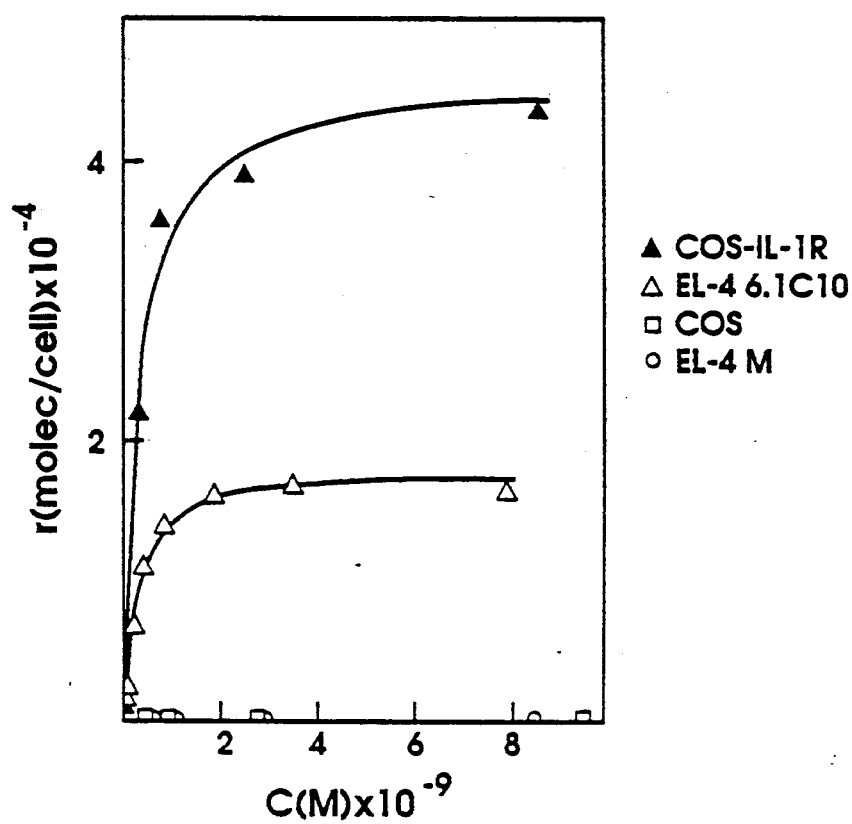
FIG. 7A compares direct binding of $^{125}$I-IL-1α to cells expressing native IL-1 receptor (EL4 6.1 C10) or recombinant receptor (COS-IL-1R)
Figure 7B:
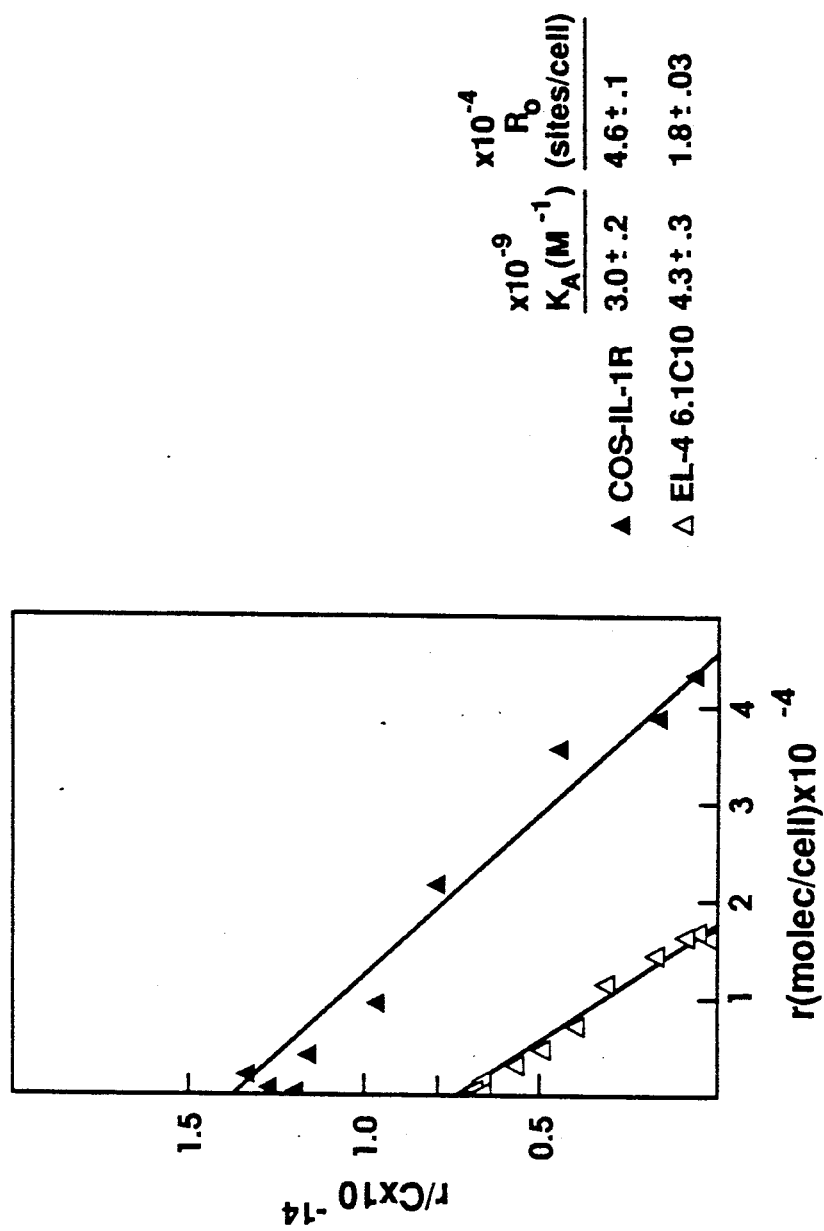
FIG. 7B shows the data from FIG. 7A replotted in the Scatchard coordinate system.
Figure 7C:
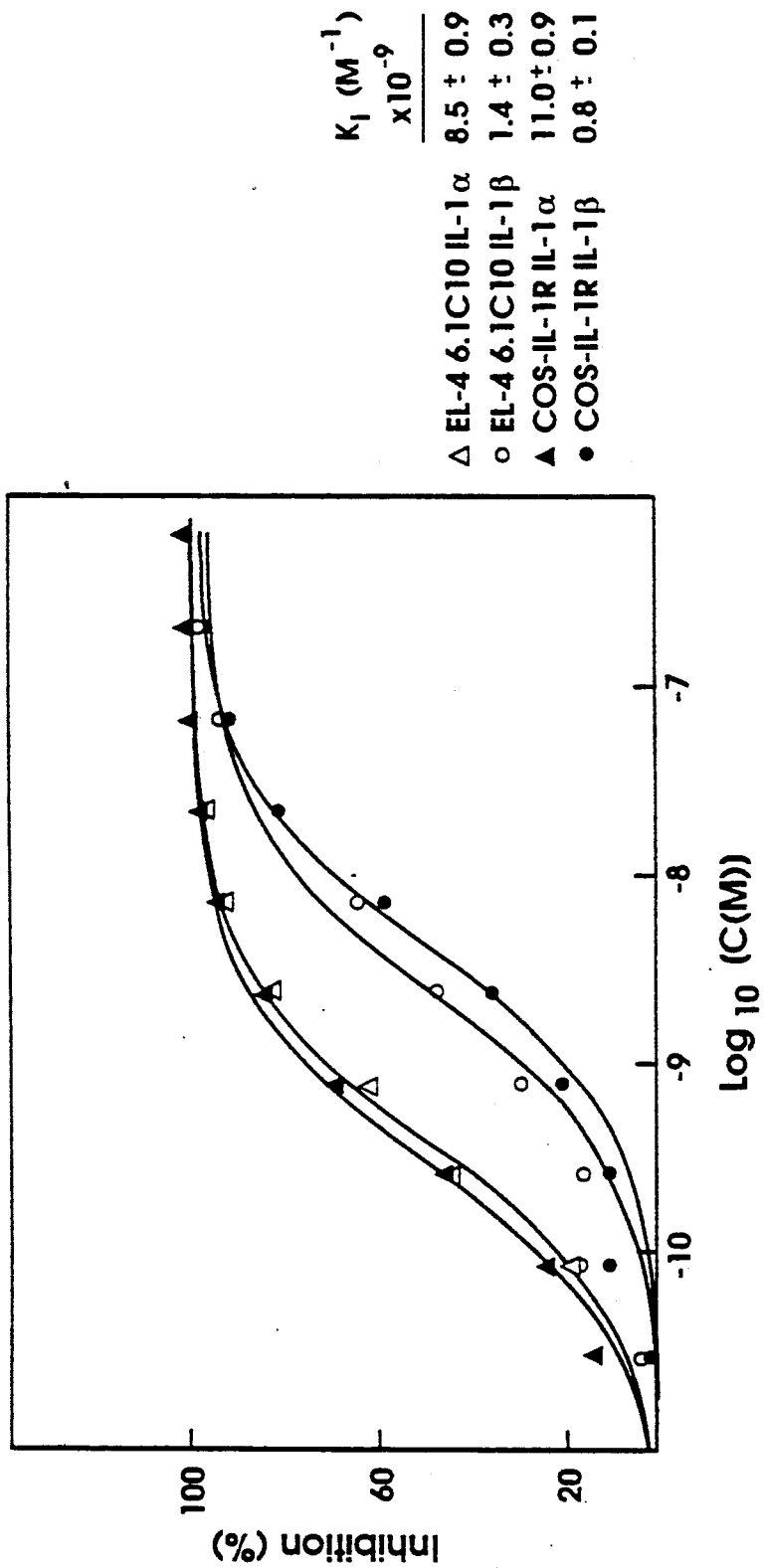
FIG. 7C indicates competition for $^{125}$I-IL-1α binding by unlabeled IL-1α and IL-1β.

The DNA from clone 78, when transfected into COS cells, led to expression of IL-1 binding activity which was virtually identical to that displayed by EL-4 6.1 C10 cells, as shown in FIGS. 7A-7C.

For binding assays, COS cells were resuspended at $1.7 \times 10^6$ cells/ml with EL-4M ($1.5 \times 10^7$ cells/ml) cells as carriers. EL-4M and EL-4 6.1 C10 were resuspended at $1.5 \times 10^7$ cells/ml. All cell suspensions were made and binding assays done in RPMI 1640/10% BSA/0.1% sodium azide/20 mM HEPES pH 7.4. Binding incubations with $^{125}$I-IL-1α or $^{125}$I-IL-1β and unlabeled IL-1α and IL-1β were done as described elsewhere in the specification. $^{125}$I-IL-1α bound to the transfected COS cells with a $K_a$ of $3.0 \pm 0.2 \times 10^9$ M$^{-1}$ (FIG. 7B). The $K_a$ for the native receptor on EL-4 6.1 C10 cells was $4.3 \pm 3 \times 10^9$M$^{-1}$. All of the binding was to recombinant receptors (see FIG. 7A); the parental COS cell population did not bind detectable $^{125}$I-IL-1α in this experiment.

In a cold competition experiment, free $^{125}$I-IL-1α concentration was $7.72 \pm 0.13 \times 10^{-10}$ M. On the transfected COS cells the maximal binding was $2.98 \pm 0.3 \times 10^4$ molecules/cell (no inhibition) and the background (measured in the presence of $6 \times 10^{-7}$M unlabeled IL-1α) was $921 \pm 60$ molecules/cell (100% inhibition). On the EL-4 6.1 C10 cells maximal binding was $1.33 \pm 0.02 \times 10^4$ molecules/cell and background (see above) was $47 \pm 2$ molecules/cell. Binding of $^{125}$I-IL-1α, both to the transfected COS cells and to EL-4 6.1 C10 cells, could be competed completely by an excess of either unlabeled IL-1α or IL-1β (FIG. 7C). The inhibition constants for IL-1α and for IL-1β were very similar with each cell type (FIG. 7C).

EXAMPLE 7

Preparation of Monoclonal Antibodies to IL-1R

Preparations of purified recombinant IL-1R, for example, human IL-1R, or transfected COS cells expressing high levels of IL-1R are employed to generate monoclonal antibodies against IL-1R using conventional techniques, for example, those disclosed in U.S. Pat. No. 4,411,993. Such antibodies are likely to be useful in interfering with IL-1 binding to IL-1 receptors, for example, in ameliorating toxic or other undesired effects of IL-1.

To immunize mice, IL-1R immunogen is emulsified in complete Freund's adjuvant and injected in amounts ranging from 10-100 μg subcutaneously into Balb/c mice. Ten to twelve days later, the immunized animals are boosted with additional immunogen emulsified in incomplete Freund's adjuvant and periodically boosted thereafter on a weekly to biweekly immunization schedule. Serum samples are periodically taken by retro-orbital bleeding or tail-tip excision for testing by dot-blot assay, ELISA (enzyme-linked immunosorbent assay), or inhibition of binding of $^{125}$I-IL-1α to extracts of EL-4 6.1 C10 cells (as desribed above). Other assay procedures are also suitable. Following detection of an appropriate antibody titer, positive animals are given an intravenous injection of antigen in saline. Three to four days later, the animals are sacrificed, splenocytes harvested, and fused to the murine myeloma cell line NS1. Hybridoma cell lines generated by this procedure are plated in multiple microtiter plates in a HAT selective medium (hypoxanthine, aminopterin, and thymidine) to inhibit proliferation of non-fused cells, myeloma hybrids, and spleen cell hybrids.

Hybridoma clones thus generated can be screened by ELISA for reactivity with IL-1 R, for example, by adaptations of the techniques disclosed by Engvall et al., *Immunochemistry* 8:871 (1971) and in U.S. Pat. No. 4,703,004. Positive clones are then injected into the peritoneal cavities of syngeneic Balb/c mice to produce ascites containing high concentrations (>1 mg/ml) of anti-IL-1 R monoclonal antibody. The resulting monoclonal antibody can be purified by ammonium sulfate precipitation followed by gel exclusion chromatography, and/or affinity chromatography based on binding of antibody to Protein A of *Staphylococcus aureus*.

Example 8

Expression of IL-1 R in Yeast

For expression of human or murine IL-1R in yeast, a yeast expression vector derived from pIXY120 is constructed as follows. pIXY120 is identical to pYαHuGM (ATCC 53157), except that it contains no cDNA insert and includes a polylinker/multiple cloning site with an NcoI site. This vector includes DNA sequences from the following sources: (1) a large SphI (nucleotide 562) to EcoRI (nucleotide 4361) fragment excised from plasmid pBR322 (ATCC 37017), including the origin of replication and the ampicillin resistance marker for selection in *E. coli*; (2) *S. cerevisiae* DNA including the TRP-1 marker, 2μ origin of replication, ADH2 promoter; and (3) DNA encoding an 85 amino acid signal peptide derived from the gene encoding the secreted peptide α-factor (See Kurjan et al., U.S. Pat. No. 4,546,082). An Asp718 restriction site was introduced at position 237 in the α-factor signal peptide to facilitate fusion to heterologous genes. This was achieved by changing the thymidine residue at nucleotide 241 to a cytosine residue by oligonucleotide-directed in vitro mutagenesis as described by Craik, *Biotechniques*:12 (1985). A synthetic oligonucleotide containing multiple cloning sites and having the following sequence was inserted from the Asp718 site at amino acid 79 near the 3' end of the α-factor signal peptide to a SpeI site in the 2μ sequence:

pIXY120 to provide a coding sequence located in frame with respect to an intact α-factor leader sequence.

The resulting expression vectors are then purified and employed to transform a diploid yeast strain of *S. cerevisiae* (XV2181) by standard techniques, such as those disclosed in EPA 0165654, selecting for tryptophan prototrophs. The resulting transformants are cultured for expression of an hIL-1R protein as a secreted or extracted product. Cultures to be assayed for hIL-1R expression are grown in 20-50 ml of YPD medium (1% yeast extract, 2% peptone, 1% glucose) at 37° C. to a cell density of $1-5 \times 10^8$ cells/ml. To separate cells from medium, cells are removed by centrifugation and the medium filtered through a 0.45μ cellulose acetate filter prior to assay. Supernatants produced by the transformed yeast strain, or extracts prepared from disrupted yeast cells, are assayed for the presence of hIL-1R using binding assays as described above.

EXAMPLE 9

Construction, Expression and Purification of Truncated Recombinant Murine IL-1 Receptor A truncated version of the IL-1 receptor protein was produced using an expression system compatible with the HELA-EBNA1 cell line, which constitutively expresses Epstein-Barr virus nuclear antigen driven from the CMV immediate-early enhancer promoter. The expression vector used was termed HAV-EO, a derivative of pDC201 which contains the Epstein-Barr virus origin and allows high level expression in the HELA-EBNA cell line. HAV-EO is derived from pDC201 by replacement of the adenovirus major late promoter with synthetic sequences from HIV-1 extending from the cap site of the viral mRNA, using the SV-40 early promoter

```
Asp718                                              StuI    NcoI   BamHI SmaI           SpeI
GTACCTTTGGATAAAAGAGACTACAAGGACGACGATGACAAGAGGCCTCCATGGAT...CCCCCGGGACA
    GAAACCTATTTTCTCTGATGTTCCTGCTGCTACTGTTCTCCGGAGGTACCTA...GGGGGCCCTGTGATC
                                        |←————— Polylinker —————→|
``` pBC120 also varies from pYαHuGM by the presence of a 514 bp DNA fragment derived from the single-standed phage f1 containing the origin of replication and intergenic region, which has been inserted at the Nru1 site in the pBR322 sequence. The presence of an f1 origin of replication permits generation of single-stranded DNA copies of the vector when transformed into appropriate strains of *E. coli* and superinfected with bacteriophage f1, which facilitates DNA sequencing of the vector and provides a basis for in vitro mutagenesis. To insert a cDNA, pIXY120 is digested with Asp718 which cleaves near the 3' end of the α-factor leader peptide (nucleotide 237) and, for example, NcoI which cleaves in the polylinker. The large vector fragment is then purified and ligated to a DNA fragment encoding the protein to be expressed.

To create a secretion vector for expressing human IL-1R, a cDNA fragment including the complete open reading frame encoding hIL-1R is cleaved with an appropriate restriction endonuclease proximal to the N-terminus of the mature protein. An oligonucleotide or oligonucleotides are then synthesized which are capable of ligation to the 5' and 3' ends of the hIL-1R fragment, regenerating any codons deleted in isolating the fragment, and also providing cohesive termini for ligation to to drive expression of the HIV-1 tat gene.

The expression construct for the soluble truncated IL-1 receptor was generated in a series of steps. The entire coding region of the receptor and part of the 5' untranslated region were removed from the original IL-1 receptor clone 78 by digestion with Asp 718 and NdeI. This fragment, containing no 3' untranslated sequences, was cloned into HAV-EO, to generate HAV-EO-FL9. A variant of this plasmid, containing a translational stop codon immediately following the codon for proline 316 and lacking all the coding sequence 3' to this, was subsequently constructed by standard methods and termed HAV-EO-MEXT.

HAV-EO-MEXT vector DNA was introduced into HELA-EBNA cells by a modified polybrene transfection as disclosed by Kawai and Nishizawa (*Mol. Cell Biol.* 4:1172, 1984). $1.5 \times 10^6$ cells were seeded into 10 ml DMEM+10% FCS, in a 10 cm tissue culture dish. Cells were incubated at 37° C., 10% $CO_2$ for 16 hours. The media was then removed and 3 ml of serum-free DMEM containing 10 μg/ml DNA and 30 μg/ml polybrene (Sigma) were added. Dishes were then incubated at 37° C./10% $CO_2$ for a further six hours, at which time the DNA mix was removed and cells were glycerol shocked by addition of 3 ml serum-free DMEM+25% glycerol (v/v) for one minute. Glycerol was removed, and the cells were washed twice with medium. Ten ml of DMEM+10% FCS were then added, and the cells were incubated at 37°/10% $CO_2$ for 18 hours.

Transfected cells were then removed with trypsin and split in a ratio of 1:9 into T175 $cm^2$ flasks (to give approximately 10% confluence) containing 25 ml DMEM+1% FCS. Supernatants containing transiently expressed soluble murine IL-1 receptor were harvested every 24 hours for up to ten days.

IL-1α binding activity in the medium was measured by inhibition of $^{125}$IL-1α to EL4 6.1 C10 cells as described by Mosley et al. (J. Biol. Chem. 262:2941, 1987) with the exception that labeled IL-1α ($2 \times 10^{-11}$, 50 μl was first incubated with the test sample (50 μl) for two hours at 8° C., prior to addition of cells ($2.5 \times 10^6$ cells, 50 μl). Each test sample was assayed at six dilutions (X3) and the inhibition dose response curve used to assess the relative inhibitory titer.

Soluble IL-1 receptor was purified from culture supernatants as described for natural receptor by Urdal et al. (J. Biol. Chem. 263:280, 1988). Culture supernatants were passed over a 1 ml bed volume IL-1α column, the column was washed with PBS and eluted with 0.1M glycine-HCl. Acid eluate fractions were immediately neutralized and subsequently tested for IL-1 binding activity using the radioreceptor inhibition assay. SDS-polyacrylamide gel electrophoresis of the material eluted by the acid treatment showed that it contained two bands of $M_r$ 60,000 and 54,000. N-glycanase treatment of this material indicated that the size heterogeneity is due to differences in N-linked glycosylation between the two species. Soluble IL-1 receptor retains full IL-1 binding activity.

We claim:

1. A homogeneous biologically active human or murine Type I Interleukin-1 Receptor of the type whose mature full length form has a Molecular Weight of about 82,000 daltons as determined by SDS-PAGE and which exhibits IL-1 binding activity.

2. A homogeneous biologically active Type I Interleukin-1 Receptor according to claims 1, consisting essentially of murine Type I Interleukin-1 Receptor.

3. A homogeneous biologically active Type I Interleukin-1 Receptor according to claim 1, consisting essentially of human Type I Interleukin-1 receptor.

4. A protein comprising a human or murine Type I Interleukin-1 Receptor of the type whose mature full length as a Molecular Weight of about 82,000 daltons as determined by SDS-PAGE which is produced by recombinant cell culture and having a specific binding activity of at least about 0.01 nanamole IL-1/nanomole Type I Interleukin-1 Receptor.

5. A homogeneous protein according to claim 4, wherein the Type I Interleukin-1 Receptor comprises the amino acid sequence of residues 1–319 in FIGS. 3A–3C.

6. A homogeneous protein according to claim 4, wherein the Type I Interleukin-1 Receptor comprises the amino acid sequence of residues 1–319 in FIGS. 5A–5C.

7. A homogeneous protein according to claim 1, consisting essentially of a substantially homogeneous protein comprising murine Type I Interleukin-1 Receptor in the form of a glycoprotein having a Molecular Weight of about 82,000 daltons as determined by SDS-PAGE, a binding affinity ($K_a$) for human IL-1α of from $3-6 \times 10^9$M, and the N-terminal amino acid sequence $NH_2$-Leu-Glu-Ile-Asp-Val-Cys-Thr-Glu-Tyr-Pro-Asn-Gln-Ile-Val-Leu-Phe-Leu-Ser-Val-Asn-Glu-Ile-Asp-Ile-Arg-Lys.

8. A homogeneous protein according to claim 4, wherein the Type I Interleukin-1 receptor is without native mammalian glycosylation.

9. A composition for regulating immune or inflammatory responses in a mammal, comprising an effective amount of human or murine Type I Interleukin-1 receptor protein composition according to claim 4, and a suitable diluent or carrier.

10. A composition for regulating immune or inflammatory responses in a mammal, comprising an effective amount of a Type I Interleukin-1 receptor protein composition according to claim 6, and a suitable diluent or carrier.

11. A protein according to claim 1 lacking a transmembrane region and intracellular domain.

12. A composition comprising homogeneous biologically active human or murine Type I Interleukin-1 receptor of the type whose mature full length form has a Molecular Weight of about 82,000 daltons as determined by SDS-PAGE, which exhibits IL-1 binding activity, and a suitable diluent or carrier.

13. A homogeneous biologically active Type I Interleukin-1 Receptor composition according to claim 12, consisting essentially of murine Type I Interleukin-1 Receptor, and a suitable diluent or carrier.

14. A homogeneous biologically active Type I Interleukin-1 Receptor composition according to claim 12, consisting essentially of human Type I Interleukin-1 Receptor, and a suitable diluent or carrier.

15. A protein composition comprising a human or murine Type I Interleukin-1 Receptor, which is produced by recombinant cell culture and having a specific binding activity of at least about 0.01 nanomole IL-1/nanomole Type I Interleukin-1 Receptor, and a suitable diluent or carrier.

16. A composition according to claim 15, wherein the Type I Interleukin-1 Receptor comprises an amino acid sequence of residues 1–319 in FIGS. 3A–3C.

17. A composition according to claim 15, wherein the Type I Interleukin-1 Receptor comprises an amino acid sequence of residues 1–319 of FIGS. 5A–5C.

18. A composition according to claim 12, consisting essentially of a substantially homogeneous protein, comprising murine Type I Interleukin-1 Receptor in the form of a glycoprotein having a molecular weight of about 82,000 as determined by SDS-PAGE, a binding affinity ($K_a$) for human IL-1α of from $3-6 \times 10^9$, and the N-terminal amino acid sequence of $NH_2$-Leu-Glu-Ile-Asp-Val-Cys-Thr-Gly-Tyr-Pro-Asn-Gln-Ile-Val-Leu-Phe-Leu-Ser-Val-Asn-Glu-Ile-Asp-Ile-Arg-Lys.

19. A composition according to claim 15 wherein the Type I Interleukin-1 Receptor is without native mammalian glycosylation.

20. A composition according to claim 12 lacking a transmembrane region and intracellular domain.

* * * * *